United States Patent
Kidron et al.

(10) Patent No.: US 7,297,965 B2
(45) Date of Patent: Nov. 20, 2007

(54) METHOD AND APPARATUS FOR SAMPLE FORMATION AND MICROANALYSIS IN A VACUUM CHAMBER

(75) Inventors: Eitan Kidron, Hod Hasharon (IL); Dror Shemesh, Hod Hasharon (IL)

(73) Assignee: Applied Materials, Israel, Ltd., Rehovot (IL)

( * ) Notice: Subject to any disclaimer, the term of this patent is extended or adjusted under 35 U.S.C. 154(b) by 91 days.

(21) Appl. No.: 11/119,207

(22) Filed: Apr. 28, 2005

(65) Prior Publication Data

US 2006/0011868 A1 Jan. 19, 2006

Related U.S. Application Data

(60) Provisional application No. 60/588,272, filed on Jul. 14, 2004.

(51) Int. Cl.
*G21K 5/10* (2006.01)
(52) U.S. Cl. .................. 250/492.2; 250/307; 250/311; 250/306; 250/492.1; 250/492.21
(58) Field of Classification Search ..................... None
See application file for complete search history.

(56) References Cited

U.S. PATENT DOCUMENTS

| | | | |
|---|---|---|---|
| 5,561,293 A | 10/1996 | Peng et al. | |
| 5,770,861 A | 6/1998 | Hirose et al. | |
| 5,783,830 A | 7/1998 | Hirose et al. | |
| 6,794,663 B2 * | 9/2004 | Shichi et al. | 250/492.21 |
| 6,858,851 B2 * | 2/2005 | Tomimatsu et al. | 250/442.11 |
| 7,002,152 B2 * | 2/2006 | Grunewald | 250/311 |
| 2002/0050565 A1 | 5/2002 | Tokuda et al. | |
| 2003/0183776 A1 | 10/2003 | Tomimatsu et al. | |

\* cited by examiner

*Primary Examiner*—Jack I. Berman
*Assistant Examiner*—Zia R. Hashmi
(74) *Attorney, Agent, or Firm*—Tarek N. Fahmi

(57) ABSTRACT

Methods and apparatus are disclosed for forming a sample of an object, extracting the sample from the object, and subjecting this sample to microanalysis including surface analysis and electron transparency analysis in a vacuum chamber. In some embodiments, a method is provided for imaging an object cross section surface of an extracted sample. Optionally, the sample is iteratively thinned and imaged within the vacuum chamber. In some embodiments, the sample is situated on a sample support including an optional aperture. Optionally, the sample is situated on a surface of the sample support such that the object cross section surface is substantially parallel to the surface of the sample support. Once mounted on the sample support, the sample is either subjected to microanalysis in the vacuum chamber, or loaded onto a loading station. In some embodiments, the sample is imaged with an electron beam substantially normally incident to the object cross section surface.

14 Claims, 38 Drawing Sheets

Needle orientation (1,1,1)

0° rotation

60° rotation

120° rotation

90° rotation

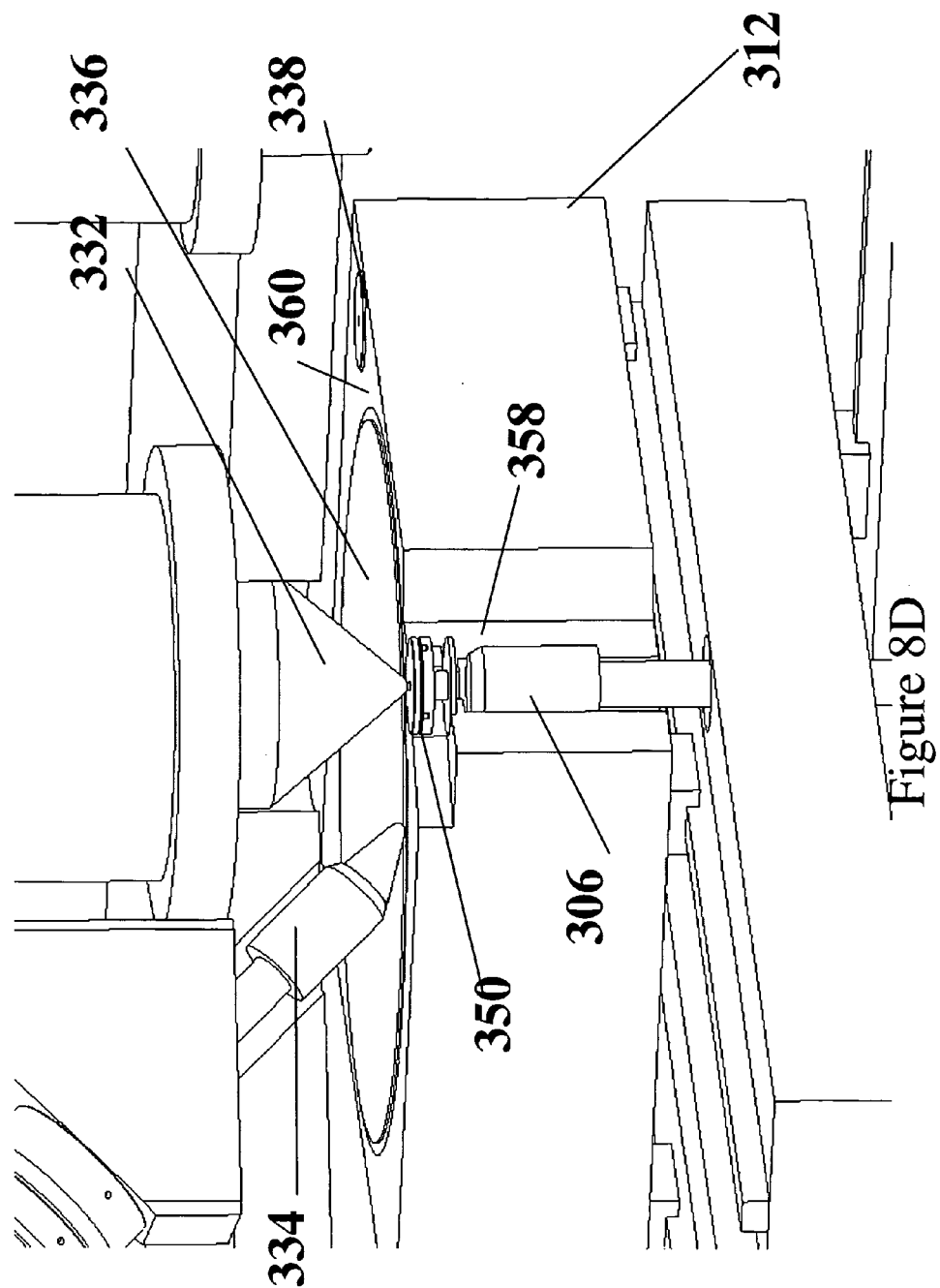

METHOD AND APPARATUS FOR SAMPLE FORMATION AND MICROANALYSIS IN A VACUUM CHAMBER

CROSS-REFERENCE TO RELATED APPLICATIONS

This application claims priority to U.S. Provisional Application Ser. No. 60/588,272, filed Jul. 14, 2004, which is incorporated herein by reference in its entirety.

FIELD OF THE INVENTION

The present invention relates generally to semiconductor device monitoring, and specifically to the preparation and imaging of thin samples for testing internal structure of fabricated devices.

BACKGROUND OF THE INVENTION

In the study of electronic materials and processes for fabricating such materials into an electronic structure, a specimen of the electronic structure is frequently used for microscopic examination for purposes of failure analysis and device validation. For instance, a specimen of an electronic structure such as a silicon wafer is frequently analyzed in scanning electron microscope (SEM) and transmission electron microscope (TEM) to study a specific characteristic feature in the wafer. Such characteristic feature may include the circuit fabricated and any defects formed during the fabrication process. An electron microscope is one of the most useful equipment for analyzing the microscopic structure of semiconductor devices.

In preparing specimens of an electronic structure for electron microscopic examination, various polishing and milling processes can be used to section the structure until a specific characteristic feature is exposed.

As device dimensions are continuously reduced to the sub-half-micron level, the techniques for preparing specimens for study in an electron microscope have become more important. The conventional methods for studying structures by an optical microscope cannot be used to study features in a modem electronic structure due to the unacceptable resolution of an optical microscope.

In the focused ion beam (FIB) technique, focused ion beam is used to either locally deposit or remove materials. Typical ion beams have a focused spot size of smaller than 100 nm when produced by a high intensity source. Sources of such high intensity ions can be either liquid metal ion sources or gas field ion sources. Both of these sources have a needle type form that relies on field ionization or evaporation to produce the ion beam. After the ion beam is produced, it is deflected in a high vacuum and directed to a desired surface area. The focused ion beams can be suitably used in the semiconductor processing industry in a cutting or attaching method to perform a circuit repair, a mask repair or a micromachining process. A cutting process is normally performed by locally sputtering a surface with a focused ion beam.

In an ion beam milling process, a material is selectively etched by a beam of ions such as $Ga^+$ focused to a sub-micron diameter, the technique is often referred to as focused ion beam etching or milling. FIB milling is a very useful technique for restructuring a pattern on a mask or an integrated circuit, and for diagnostic cross-sectioning of microstructures. In a typical FIB etching process, a beam of ions such as $Ga^+$ is incident onto a surface to be etched and the beam is deflected to produce a desirable pattern. The focused ion beam can be used to bombard a specimen surface such that a cavity is formed on the surface of an electronic structure to review a characteristic feature of the structure for electron microscopic examination. The FIB technique utilizes a primary beam of ions for removing a layer of material at a high current, and for observing the surface that was newly formed at a low current. The observation of the surface is made by detecting the secondary electrons emitted from the sample surface when the surface is bombarded by the ions. A detector is used to receive the secondary electrons emitted from the surface to form an image. Even though the FIB method can not produce an image of a high resolution like that obtainable in a SEM/TEM, the FIB method can be used to sufficiently identify a newly formed cross-sectional surface which may contain the characteristic feature to be examined. The capability of the FIB technique for making observations down to a resolution of 5~10 nm enables the cutting of a precise plane in an electronic structure such that the electronic structure may be later examined by a SEM or TEM technique at a higher resolution than that capable with FIB.

Although TEM techniques can provide a higher resolution image and a more detailed description of the internal structure of a than is available using SEM techniques, they are only effective for electron transparent samples. Thus it is a basic requirement for TEM samples that the sample must be thin enough to be penetrated by the electron beam and thin enough to avoid multiple scattering, which causes image blurring. Nonetheless, it is recognized in the art that thin samples extracted from wafers may be brittle, and subject to fracture or crumbling. Furthermore, the fragile nature of thin extracted samples means that processes for extracting thin samples are difficult to automate, thus hindering efforts to automate these processes. There is an ongoing need for reliable and automated techniques for the obtaining and imaging of TEM samples to make TEM sampling a viable part of semiconductor analysis and manufacturing.

An additional technique for conducting electron transparency analysis with nanometer level spatial resolution is scanning transmission electron microscopy (STEM). The TEM is an apparatus in which an electron beam is irradiated onto a sample, and the transmitted electron beam is magnified using a lens. On the other hand, the STEM is an apparatus in which an electron beam is focused onto a micro-area, and a two-dimensional image is obtained by measuring intensities of the transmitted electron beam while the electron beam is being scanned on the sample. US 20030127595, incorporated herein by reference, discloses methods and apparatus for scanning transmission electron microscopy.

Enabled by automated, multicolumn tools combining SEM and FIB in a single device, automated techniques for the obtaining and imaging of SEM samples are already well known and are employed in the automated reviewing of defects and for process monitoring. Examples of commercially available models of such multicolumn tools include SEMVision™ G2 FIB (Applied Materials, Santa Clara, Calif.) and the DualBeam™ (FEI Company, Hillsboro, Oreg.). It is noted that the SEMVision™ G2 FIB is also used in process control.

Below is enumerated a list of United States Patents, published United States Patent applications that disclose potentially relevant background material. Each of the following United States Patents and published United States Patent application are incorporated herein by reference in their entirety:

U.S. Pat. No. 6,194,720 of Li et al., titled "Preparation of Transmission Electron Microscope Samples";

U.S. Pat. No. 6,670,610 of one of the present inventors and coworkers, titled "System and Method for Directing a Miller";

U.S. Pat. No. 6,700,121 of Kelly et al., titled "Methods of Sampling Specimens for Microanalysis";

U.S. published patent application 2001/0044156 of Kelly et al., titled "Methods of Sampling Specimens for Microanalysis";

U.S. published patent application 2001/0045511 of Moore et al, titled "Method For Sample Separation and Lift-Out";

U.S. published patent application 2002/0000522 of Alani, titled "Ion Beam Milling System and Method for Electron Microscopy Specimen Preparation";

U.S. published patent application 2002/0121614 of Moore et al, titled "Total Release Method for Sample Extraction from a Charged-Particle Instrument";

U.S. published patent application 2004/0245466 of Robinson et al, titled "Transmission electron microscope sample preparation";

U.S. published patent application 2004/0129897 of Adachi et al., titled "Sample manufacturing apparatus";

U.S. published patent application 2004/0164242 of Grunewald titled "Sample preparation for transmission electron microscopy";

U.S. published patent application 2004/0246465 of Iwasaki et al. titled "Micro-sample pick-up apparatus and micro-sample pick-up method";

U.S. published patent application 2004/0178355 of Rasmussen titled "Sample Manipulation System".

Presently, in most semiconductor manufacturing facilities, electron transparency samples of semiconductor wafers for microscopy analysis are obtained on site, and subsequently shipped to an electron microscopy laboratory for electron transparency analysis.

Time delayed process monitoring and defects identified in a manufacturing process only after a certain time delay could be expensive for a semiconductor manufacturer, and thus it is desirable that defective manufacturing processes be identified as soon as possible and preferably on site.

There is an ongoing need for methods and systems for extracting samples from wafers for electron transparency microanalysis. Preferably, such methods would be implementable in a single tool. More preferably, such methods would be automated within a single tool, in order facilitate their integration into the semiconductor manufacturing process. Preferably, such methods would allow for extraction of a sample without boring a hole in the wafer, splitting the wafer, or otherwise rendering the semiconductor wafer unusable after sample extraction.

Furthermore, it is recognized that in the context of defect analysis and process control analysis, it is often necessary to image a cross section surface of a sample of a wafer. Thus, there is an ongoing need for techniques for microanalyzing cross sections of samples that contain characteristic features.

SUMMARY OF THE INVENTION

The aforementioned needs are satisfied by several aspects of the present invention.

It is now disclosed for the first time a method and apparatus for forming and extracting a sample from an object situated in a vacuum chamber and for performing electron transparency analysis on the sample within the vacuum chamber. The disclosed apparatus includes a vacuum chamber, an ion beam source for forming the sample, a robotic manipulator for extracting and manipulating the sample, and a first electron microscopy device for imaging the sample such that at least a first portion of the electron beam traverses at least a portion of the sample.

According to many embodiments, the ion beam source, the robotic manipulator, and the first electron microscopy device are all at least partly situated within the vacuum chamber.

According to some embodiments, the apparatus further includes at least one stage for supporting the object and optionally the sample.

In some embodiments, the stage includes a support surface configured to support a 200 mm or larger wafer.

In some embodiments, the stage includes a support surface with a surface area of at least 30,000 square millimeters.

In some embodiments, one stage is provided for supporting both the object and the sample. In other embodiments, one stage is provided for supporting the object, and a separate stage is provided for supporting the sample. In further embodiments, only one stage is provided for the object only, and the sample is subjected to electron transparency analysis while attached to and supported by a probe or needle.

According to some embodiments, at least one stage is movable.

In some embodiments, the ion beam source is an ion beam column that is tiltable relative to the stage supporting the object.

According to some embodiments, the first electron microscopy device includes an electron beam source for emitting the electron beam and an electron detector for detecting electrons derived from the first portion of the electron beam which traverses at least a portion of the sample, each at least partly situated inside the vacuum chamber. In some embodiments, the electron beam source and electron detector are situated on opposite sides of the upper surface of the stage supporting the sample.

According to some embodiments, the electron beam source is configured to emit the electron beam at an energy sufficiently high to traverse an electron thin specimen.

In some embodiments, the first electron microscopy device is a STEM device. Alternatively, the first electron microscopy device is a TEM device.

Optionally, the presently disclosed apparatus further includes a detector for surface analysis of the extracted sample. Thus, some embodiments further provide at least one additional electron detector for detecting electrons derived from an electron scattering off of a surface of the extracted sample. In some embodiments, the electron detector is operative to detect electrons derived from the scattering of a second portion of the electron beam off of a surface of the extracted sample. In a particular embodiment, the first electron microscopy device includes an SEM electron column, an STEM detector, and an SEM detector for detecting secondary and/or backscattered electrons.

Exemplary electrons derived from the scattering of electrons off of the surface of the sample include secondary electrons, a backscattered electrons, and auger electrons.

Optionally, the apparatus includes an x-ray detector, for detecting x-rays derived from the electron beam scattering off of the surface of the sample.

In some embodiments, the disclosed apparatus includes an optional second dedicated electron microscopy device for electron transparency analysis. In some embodiments, the first electron microscopy device is configured for both electron transparency analysis as well as surface analysis, while the second electron microscopy device is optimized for electron transparency analysis.

In some embodiments, the second electron microscopy device is a STEM device. Alternatively, the second electron microscopy device is a TEM device.

In some embodiments, the currently disclosed apparatus includes two or more electron beam sources, two or more ion beam columns, and a multiplicity of detectors.

According to some embodiments, a controller is operatively coupled to at least one element selected from the ion beam source, the electron microscopy device, the second electron microscopy device, the robotic manipulator, and a motor controlling the movement of a stage. In one particular embodiment, the controller is programmed to perform at least one method disclosed herein for electron transparency analysis of a sample formed from the object and optionally mounted on a sample support.

According to some embodiments, the robotic manipulator includes a probe or needle that is reversibly attachable to the sample.

According to some embodiments, the electron microscopy device includes a transmission electron microscopy device. Alternately, the electron microscopy device includes a scanning transmission electron microscopy device.

According to some embodiments, the apparatus further includes at least one charged particle detector such as an ion detector or electron detector situated to detect ions and/or electrons derived from subjecting the sample or the object to the ion beam.

In many embodiments, it is desired to subject an extract sample to surface analysis within the same tool in which the sample is formed from an object. Exemplary surface analysis techniques include SEM imaging, detection of x-rays and auger electrons.

It is now disclosed for the first time apparatus for forming, extracting and imaging a sample of a wafer, including a vacuum chamber, an ion beam source for forming the sample, at least partly situated within the vacuum chamber, a robotic manipulator for extracting and manipulating the sample, at least partly situated within the vacuum chamber, an electron beam source for scattering a beam of electrons off of surface of the sample, and an auger electron detector, for detecting auger electrons derived from subjecting the sample to the beam of electrons.

It is now disclosed for the first time apparatus for forming, extracting and imaging a sample of a wafer, including a vacuum chamber, an ion beam source for forming the sample, at least partly situated within the vacuum chamber, a robotic manipulator for extracting and manipulating the sample, at least partly situated within the vacuum chamber, an electron beam source for scattering a beam of electrons off of surface of the sample, and an x-ray detector, for detecting x-rays derived from subjecting the sample to the beam of electrons.

In accordance with some embodiments of the present invention, a method of sample formation and imaging within a vacuum chamber is provided. This method includes placing an object into a vacuum chamber, forming a sample from the object and imaging the sample such that at least a portion of an electron beam traverses at least a portion of the sample. It is noted that in some embodiments, the forming and imaging are carried out in the vacuum chamber.

According to some embodiments, the object is a substantially cylindrically shaped object such as a semiconductor wafer. According to other embodiments, the object is a prismatic object such as a die.

According to some embodiments, the object is penetrated to a depth of at most 10% of a thickness of the object during the stage of forming. According to other embodiments, the object is penetrated to a depth of at most 3%, 5%, 20%, or 50% of a thickness of the object during the stage of forming.

According to some embodiments, the formed sample is situated onto a sample support and imaged in situ while situated on the sample support. According to some embodiments, the situating is effected using a robotic manipulator.

According to some embodiments, the stage of forming includes focused ion beam or electron beam milling. According to some embodiments of the present invention, the stage of forming excludes mechanical cleaving. According to some embodiments of the present invention, the stage of forming excludes laser cutting.

According to some embodiments, the stage of forming includes a beam milling selected from the group consisting of ion beam milling and electron beam milling.

Not wishing to be bound by theory, it is now disclosed that methods for sample formation wherein the stage of forming includes ion beam milling and excludes mechanical cleaving are desirable because they damage the wafer only in the vicinity of the area from where the sample is extracted.

According to particular embodiments, the stage of forming includes cutting a first cut into the object using an ion beam, the first cut at least partially surrounding a target location on a surface of the object and cutting a second cut in the object, using the ion beam, at an acute angle to a plane of the object, thereby undercutting the target location.

Optionally, the stage of forming includes tilting the FIB column relative to a stage upon which the object is situated. Alternatively or additionally, the stage itself is tilted.

In some embodiments, the stage of forming includes rotating the object within the object plane.

According to particular embodiments, the sample support includes at least one aperture. According to particular embodiments, the electron beam traverses at least a portion of one the aperture. According to particular embodiments, at least part of the sample is situated over the aperture.

According to some embodiments, the imaging includes imaging an object cross section surface of the sample. According to some embodiments, the sample is imaged such that the electron beam is incident substantially normally to the object cross section surface of the sample. Not wishing to be bound by theory, it is now disclosed that imaging the object cross section surface of the sample in some embodiments reveals details of the internal structure of a cross section of the object, and is useful in defect analysis.

According to some embodiments, the sample is situated on a surface of the sample support such that an object cross section surface of the sample is substantially parallel to the surface of the sample support. Not wishing to be bound by theory, it is now disclosed that situating the sample on the sample support with this orientation is useful in certain situations where it is desired to subsequently subject the cross section surface to a particle beam with a predetermined orientation relative to the cross section surface.

According to some embodiments, the sample includes a segment having two substantially parallel surfaces.

According to some embodiments, the sample comprises a segment having two substantially parallel surfaces that are substantially perpendicular to the outer surface of the sample.

Optionally, after the sample mounted on the sample support the sample is further thinned before and/or after imaging. In some embodiments, the sample thinning includes subjecting a object cross section surface of the sample to a focused ion beam that is incident normally to the object cross section.

According to some embodiments, the sample support includes a TEM grid.

In some embodiments, the sample support is cylindrically shaped and includes exactly one aperture.

The sample support includes any appropriate material known in the art. Appropriate materials include but are not limited to copper, nickel, molybdenum, and platinum.

In yet other embodiments, the sample support is other than a TEM grid, preferably a mostly solid flat support where less than the overwhelming majority of the upper surface of the sample support is occupied by the at least one aperture. Not wishing to be bound by theory, it has been found that use of such a sample support stabilizes the process whereby the sample is situated on the sample support, once again obviating the need for the method to be implemented by skilled technicians.

According to some embodiments, less than about 98% of an area of the surface of the sample support is occupied by the at least one aperture. According to particular embodiments, less than about 50% of an area of the surface of the sample support is occupied by the at least one aperture.

According to some embodiments, the sample includes a segment having two substantially parallel surfaces, and the probe is affixed to the sample in a geometric orientation such that one of the parallel surfaces of the sample faces away from the object as the sample is extracted from the object and rotated.

According to some embodiments, a probe is affixed to the sample before the imaging. One exemplary location to attach the probe is to the outer surface of the formed sample.

According to some embodiments, the probe is substantially nonparallel to the outer surface.

According to some embodiments, the probe is oriented away from the outer surface. Optionally, the probe is oriented at an angle that is substantially 55 degrees from the normal vector of the outer surface of the sample.

In some embodiments, when the sample is removed from the object, it is rotated substantially 120 degrees before mounting on the sample support.

Any known technique for affixing the needle or probe is appropriate for the present invention. According to some embodiments, a tip of the needle or probe is fixed to the sample by ion-beam metal deposition. Alternately, a tip of the needle or probe is fixed to the sample by electrostatic attraction.

The probe is optionally detached from the sample before electron transparency imaging. Exemplary techniques for detaching the probe or needle include ion beam milling.

According to some embodiments, the stage of imaging includes situating the sample onto a sample support, and said probe is detached from the sample after situating.

Any shape object is appropriate for the disclosed method. Thus, in some embodiments, a sample is formed from a wafer that is substantially cylindrical. In some embodiments, a wafer is pre-cleaved before placing in the vacuum chamber to form and extract the sample. In some embodiments, the object is substantially prismatic.

It is now disclosed for the first time a method of sample and imaging including placing an object into a vacuum chamber, forming a sample from the object, and subjecting an object cross section surface of the sample to microanalysis, wherein the forming and microanalysis are carried out while the sample is in the vacuum chamber.

According to some embodiment, microanalysis includes subjecting the sample to a particle beam selected from the group consisting of an ion beam and an electron beam, wherein the particle beam is incident substantially normally to said object cross section surface.

It is now disclosed for the first time a method of extracting and mounting a sample. The disclosed method includes forming the sample from the object so that the sample includes an object cross section surface of the object, and situating at least one sample onto a surface of a sample support that includes at least one aperture so that the object cross section surface of the sample is substantially parallel to the surface of sample support.

According to some embodiments, the sample is further subjected to electron transparency analysis within the same vacuum chamber that the sample was formed from the object. Alternately, at least one mounted sample onto a loading station or cassette. Optionally the loading station or cassette can be shipped to a separate tool for electron transparency analysis.

According to some embodiments, the forming of the sample produces an indentation in the object, and the method further includes depositing material into the indentation.

According to particular embodiments, the deposition is carried in the vacuum chamber. According to particular embodiments, the indentation is completely filled by the deposited material. According to particular embodiments, the deposition includes focused ion beam deposition.

Not wishing to be bound by theory, it is now disclosed that methods provided by embodiments of the present invention cause minimal damage to a semiconductor wafer while still allowing for defect analysis and process control including electron transparency of a cross section of the wafer. Furthermore, it is now disclosed that the optional filling of the indentation with deposited material further minimizes the damage rendered to the wafer by the sampling process.

It is now disclosed for the first time a method forming a sample of an object in a vacuum chamber, and iteratively thinning and imaging the sample inside the vacuum chamber, producing a plurality of images. The disclosed method includes providing an object in a vacuum chamber, forming a sample from the object inside the vacuum chamber, thinning at least a portion of the sample with an ion beam, and imaging the thinned sample, wherein at least a portion of said sample is subjected to an electron beam.

In some embodiments, at least one said stage of imaging includes electron transparency analysis.

In some embodiments, at least one said stage of imaging includes detecting particles selected from the group consisting of secondary electrons, backscattered electrons, auger electrons, and photons.

In some embodiments, the sample is thicker than an electron transparency threshold at a time during a first stage of imaging, and the sample is electron transparent at a time during said subsequent stage of imaging.

In some embodiments, at least one stage of imaging further includes subjecting at least a portion of the sample to optical microscopy.

In some embodiments, the thinning and imaging are repeated at least once until said at least a portion of said electron microscopy specimen is eliminated by said thinning.

Any known method for thinning a sample with an ion beam is appropriate for the disclosed method. Appropriate methods include but are not limited to subjecting the sample to a focused ion beam, and subjecting the sample to a beam of argon ions from an ion gun.

In some embodiments, the thinning includes selective removal of material.

Not wishing to be bound by theory, it is disclosed the embodiments of the present invention that recite iterative thinning and electron transparency analysis of a sample are also appropriate for samples that are not necessarily electron-transparent upon removal from the wafer. This embodiment of the present invention is particularly advantageous, since more structurally sound samples are less prone to mechanical damage such as fracture upon formation or removal from the wafer. More stable samples are easier to handle, and are particularly appropriate for embodiments where the methods of sample preparation and imaging are automated.

Furthermore, it is noted that for some embodiments the optimal sample thickness for imaging is not known a priori. Thus, embodiments of the present invention provide methods for obtaining a plurality of imaging, each one reflecting a different sample thickness. In some embodiments, the alternate sample thinning and imaging are performed automatically.

In a particular embodiment, the alternate ion beam milling and electron microscopy imaging are performed in situ when the sample is mounted on a sample support. It is noted that for some embodiments, this allows for the mounting of thicker and more stable samples than would otherwise be used.

Although certain embodiments of the invention do not preclude the precleaving of an object or semiconductor wafer before sample formation, the techniques of the present invention do not require the wafer to be precleaved before extracting the samples, and do not require mechanical milling as part of the sample formation process. Embodiments and methods where the wafer is not precleaved are easier to automate, thus providing for defect analysis and process control in a manner that is minimally disruptive to the semiconductor manufacturing practice. Not wishing to be bound by theory, it is noted that obtaining samples from the wafer using methods of the present invention does only minimal damage to the wafer, leaving much of the wafer intact, and minimizing the economic impact of defect analysis on the overall cost of the manufacturing process.

The present inventors for the first time are disclosing a tool including a vacuum chamber, an ion beam source for forming a sample from an object, a robotic manipulator for extracting and manipulating a formed sample, and an electron microscopy device for performing electron transparency analysis of a sample extracted from an object within the tool. Heretofore, this automatic tool was not possible, due to the difficulties associated sample handling, and more specifically, due to difficulties with automatically removing an electron-transparent sample and mounting the sample for imaging. More specifically, the lack of a process whereby a sample of a sample can be milled to a very small thickness that is not limited by the sample transfer process from the wafer in the same vacuum chamber in which the sample is formed precluded the creation of the tool disclosed herein. Not wishing to be bound by theory, it is noted that methods of embodiments of the present invention overcome these difficulties.

These and further embodiments will be apparent from the detailed description and examples that follow.

BRIEF DESCRIPTION OF THE DRAWINGS

FIG. 8B-8E provides isometric broken illustrated views of a tool for sample formation and electron transparency analysis of the formed samples according to some embodiments of the present invention;

DETAILED DESCRIPTION OF THE INVENTION

It should be understood that the class of embodiments described herein provides only a few examples of the many advantageous uses of the innovative teachings herein. In general, statements made in the specification of the present application do not necessarily delimit any of the various claimed inventions. Moreover, some statements may apply to some inventive features but not to others.

In accordance with many embodiments of the present invention, a disclosed method for sample formation begins with cutting of a portion of an object. In one specific embodiment, the object is a semiconductor wafer, though in other embodiments, exemplary objects include a biological material, a micromechanical device, a thin film, etc.

Figure 1:
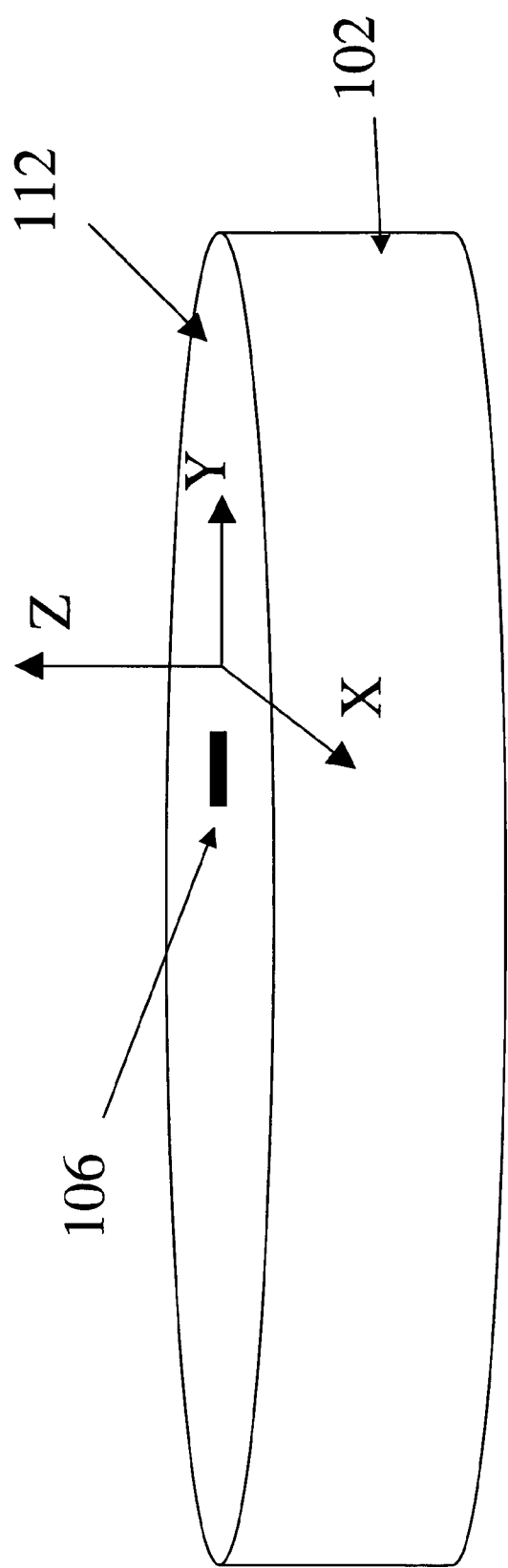
FIG. 1 provides a perspective view of a wafer from which a sample is to be obtained.

FIG. 1 provides an exemplary illustration of an object 102 from which a portion is to be extracted near a target location 106, the object 102 including an upper or outer surface 112. In FIG. 1, the object 102 depicted is of cylindrical shape, though this is by no means a limitation, and the present invention may be practiced with an object of any shape, including objects of substantially rectangular prism shape, objects of irregular dimensions, or any other shape. In some embodiments, the object 102 is a semiconductor wafer. It is noted that for many embodiments, the object 102 is a cylindrically shaped semiconductor wafer, and the relative dimensions of the diameter of the object 102 and the thickness of the object 102 as depicted in FIG. 1 is not to scale. For many such embodiments, the wafer is much thinner relative to the diameter than is shown in FIG. 1.

In many embodiments, the initial cutting penetrates the upper surface of the object 102. In particular embodiments, the target location 106 is chosen based on the presence of a particular feature of interest warranting further study using electron transparency analysis. Exemplary features include failing semiconductor devices such as capacitors made of a number of sequentially deposited layers, or a metal contact in a memory cell. In the semiconductor industry, such failing devices are commonly located through electrical-failure-site maps using various surface and voltage features. Such a feature normally would have a microstructure penetrating into the bulk of the wafer and may be surrounded by other microstructures such as other cell circuitry. For purposes of illustration, the feature of interest will be assumed to be in a Y-Z plane defined by the Z and Y axes. It will be appreciated that because the feature is included in the Y-Z plane, the Y-Z plane defines a cross-section plane of the object 102 to be exposed in specimen preparation.

Although only one target location 106 is illustrated on upper surface 112 of object 102, in various embodiments more than one target location 106 exists, and samples are extracted and imaged from multiple target locations.

After identifying the specific location 106, a sample is formed by cutting object 102 through upper surface 112. Although not a specific requirement, in many embodiments, the cutting technique includes an ion beam milling technique, preferably a focused ion beam milling technique. In the focused ion beam ("FIB") technique, an object 102 or a subsection of object 102 is mounted on a specimen holder (not shown) and conveniently placed into a focused ion beam chamber (not shown) for focused ion beam milling. It is noted that for many embodiments wherein a FIB technique is used to cut the object 102, the present invention provides methods for sample extraction wherein other portions of the object are not subjected to incidental damage. Such incidental damage is especially costly for the embodiments wherein the object 102 is a semiconductor wafer.

The FIB may be either a single-beam model, or a dual-beam model. Typical FIB instruments are those manufactured by Applied Materials (Applied Materials, Santa Clara, Calif.) including the SEMVision™ G2 FIB and those available from FEI Company of Hillsboro, Oreg., as models 200, 820, 830, or 835. The skilled practitioner is referred to U.S. Pat. No. 6,670,610 of Shemesh et al, titled "System and Method for Directing a Miller."

The X-Y plane as denoted in FIG. 1 is referred to as the "object plane."

Figure 2A:
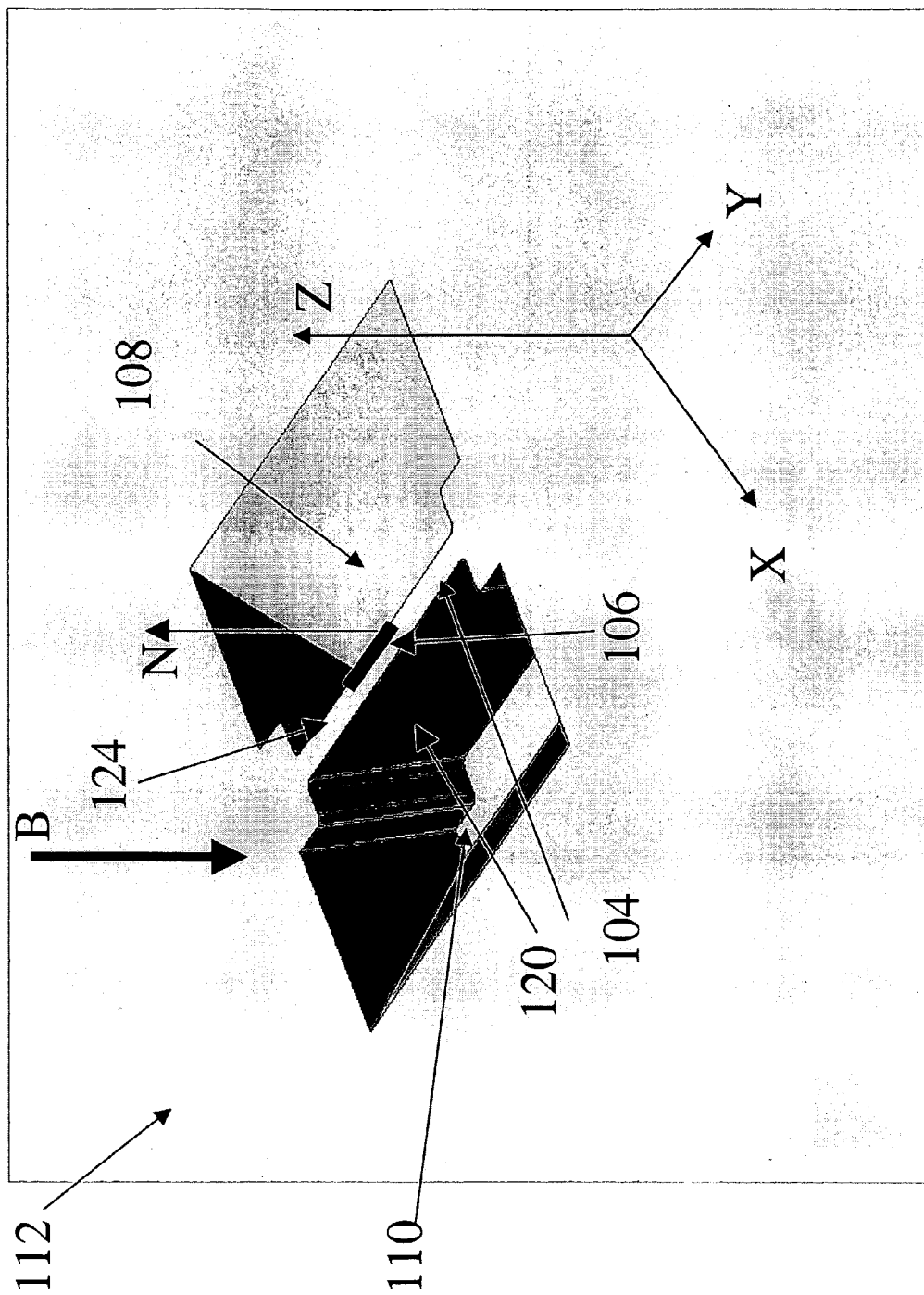
FIG. 2A provides a perspective view of an exemplary embodiment of sample formation.
Figure 2B:
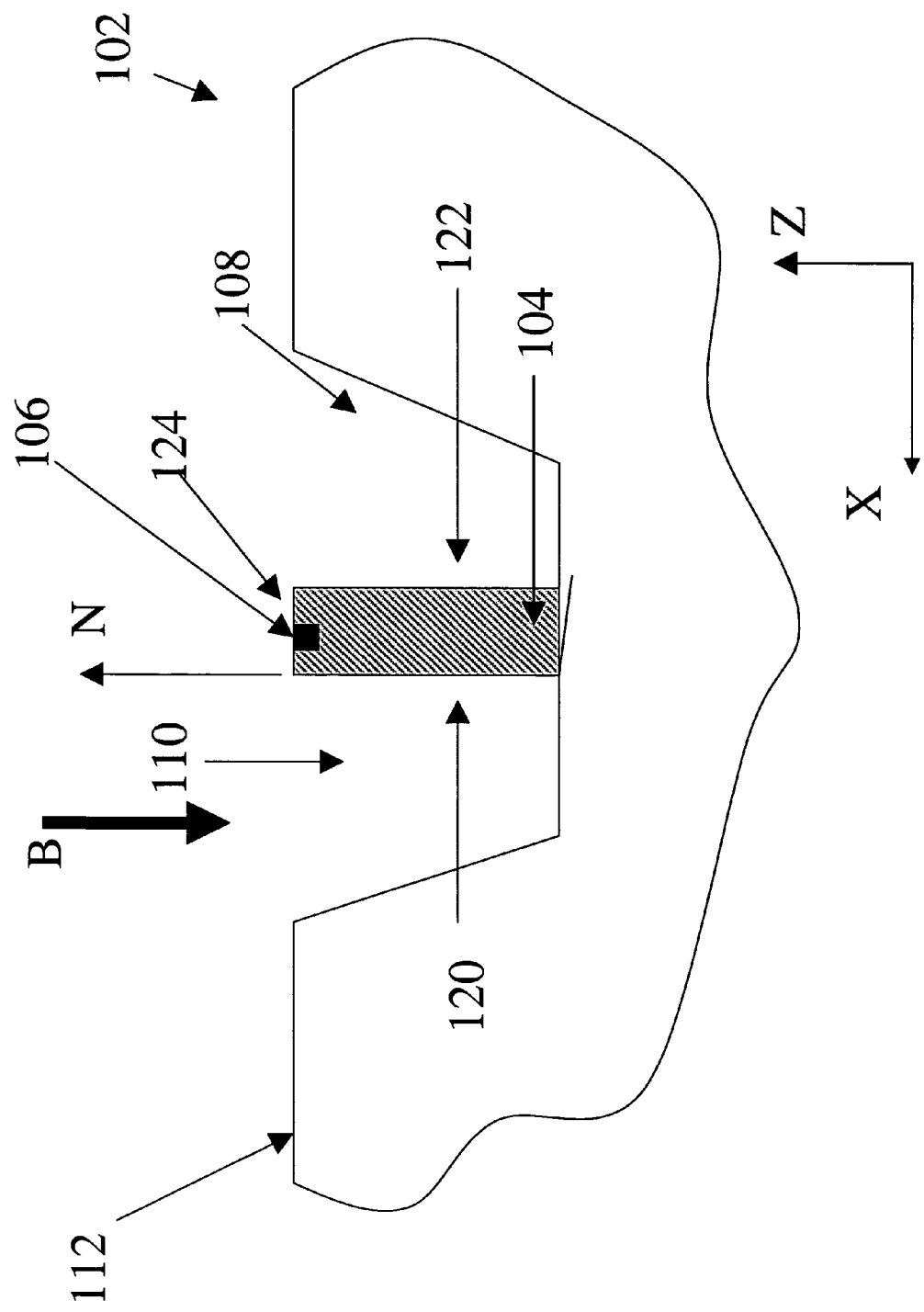
FIG. 2B provides a cross-section view of an exemplary embodiment of sample formation.
Figure 2C:
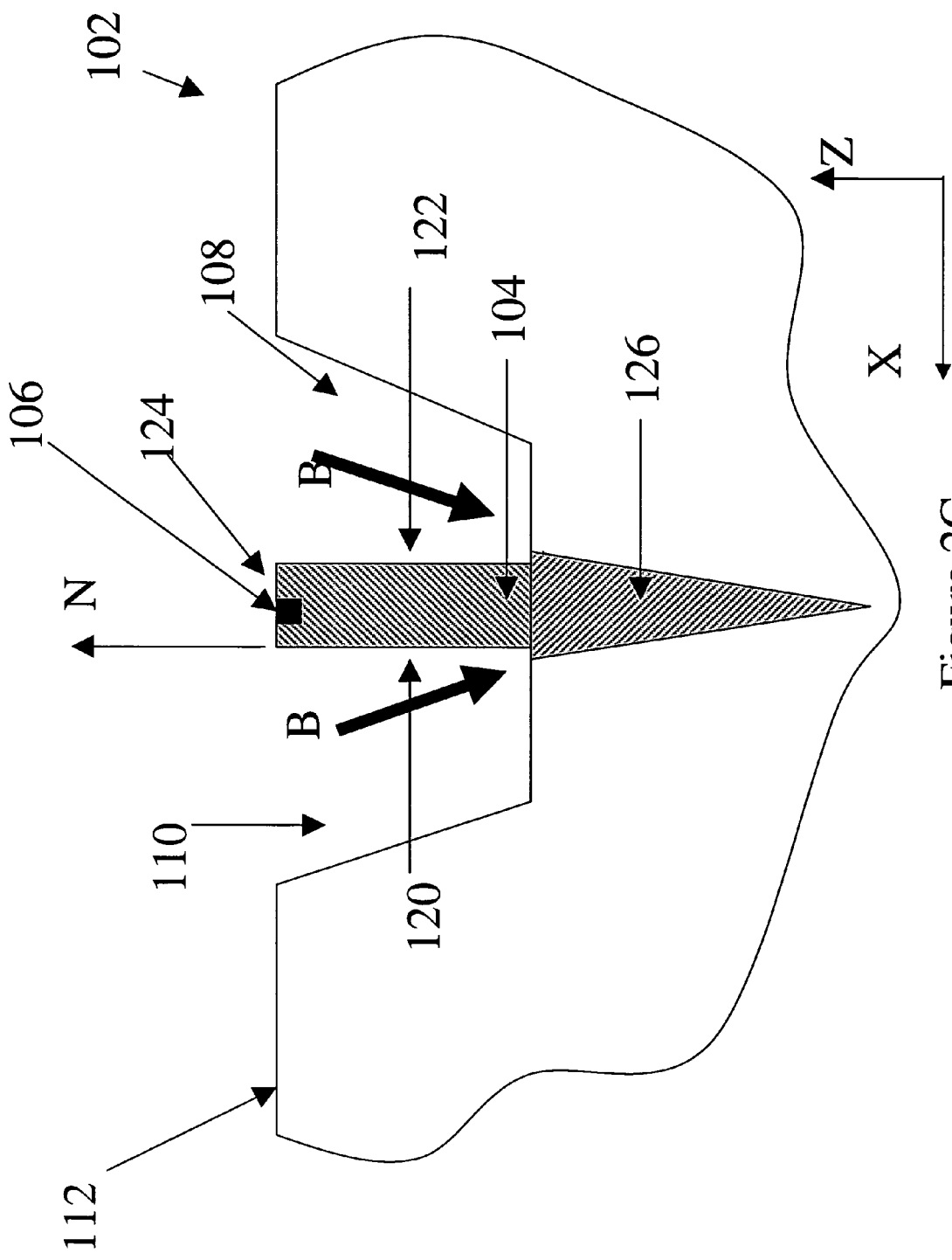
FIG. 2C provides a cross-section view of an exemplary embodiment of sample formation.

FIGS. 2A through 2C illustrate an exemplary embodiment of the present invention wherein a sample 104 is initially formed by an ion beam creating two substantially parallel trenches 110 and 108 through upper surface 112 of object 102. In FIG. 2A, the vector B represents the incident vector of the ion beam, while the vector N represents the outward normal of an outer surface 124 of sample 104. As used herein, the "outer surface" of the sample refers to a surface affixed in the sample corresponding to the upper surface 112 of the object 102. When the sample 104 is subsequently removed from the object 102 and subjected to rotation, the outer surface 124 of the sample 104 affixed therein rotates with the sample.

In the embodiments depicted in FIGS. 2A-D, sample 104 is a thin sample with two substantially parallel walls, or a membrane shaped sample, and sample 104 includes a region with a shape that is substantially a rectangular prism. In certain exemplary embodiments the width of this rectangular prism along the Y axis is ~15-20 μm, the depth of this rectangular prism along the Z axis is ~3-5 μm. In other exemplary embodiments, the depth of this rectangular prism is no more than 10 microns, in some embodiments no more than 20 microns, in some embodiments no more than 50 microns.

In some embodiments wherein it is intended to subject a portion of sample 104 to electron transparency analysis, a thickness along the X axis is 20-100 nm. Nevertheless, this thickness range should not be construed as a limitation, as embodiments of the present invention provide apparatus and methods for thinning a sample extracted from the object in the same vacuum chamber in which the sample is formed. Thus, in some embodiments where it is intended to subject a portion of sample 104 to electron transparency analysis, the thickness along the X axis is greater than 100 nm, even on the order of magnitude of a micron. For these embodiments, the sample is thinned after formation before electron transparency analysis. Not wishing to be bound by theory, it is noted that a thicker sample is it is less likely to fracture or crumble.

For embodiments where it is intended to subject the sample 104 to microanalysis other than electron transparency analysis, the sample may be of any thickness along the X axis. In some embodiments, the sample thickness is greater than 100 nm.

These aforementioned dimensions are merely exemplary values, and it is to be understood that the samples of different dimensions are also acceptable.

As illustrated in FIG. 2B, the membrane shaped sample 104 includes an outer surface 124, and proximal 120 and distal 122 object cross section surfaces. As used herein, a "sample wall" is a surface of the sample 104 affixed on the sample that is substantially perpendicular to an outer surface affixed within the sample. Examples of sample walls include proximal 120 and distal 122 object cross section surfaces. In some embodiments, a sample wall is adjacent to the outer surface.

In some embodiments, the sample comprises a segment having two substantially parallel surfaces. As used herein, an "object cross section surface" is a sample wall affixed on the sample that is substantially parallel to parallel trenches 110 and 108 upon formation of the parallel trenches. Exemplary object cross section surfaces include proximal 120 and distal 122 object cross section surfaces.

In accordance with some embodiments of the present invention, it has been found by the present inventors that it is useful to subject sample walls, more particularly object cross section surfaces to microanalysis wherein the sample wall or object cross section surface is subjected to a beam of electrons to produce a microanalysis image.

Optionally, the object cross section surface is iteratively thinned and microanalyzed, providing a plurality images wherein each image represents a different exposed object cross section surface.

It is noted for the stage of sample formation depicted in FIG. 2B, there is no fundamental difference between the proximal and distal sample walls, and the method for sample formation does not require any asymmetry in the sample geometry at this stage. Thus, the denoting of surfaces 120 and 122 as "proximal" and "distal" object cross section surfaces is arbitrary for the stage of sample formation depicted in FIG. 2B. According to some embodiments of the present invention, the proximal 120 and distal 122 object cross section surfaces are treated differently at a later stage in the sample formation and extraction process.

Subsequent to the forming of the membrane shaped sample 104, sample 104 is removed from the surrounding object 102.

Various techniques for cutting a completely formed sample and for removing the sample from the wafer are well known in the art. For example, U.S. Pat. No. 6,700,121 discloses the cutting of a sample from a larger object by forming two adjacent parallel trenches, where the sample is formed with a tether connecting the sample to the larger object. The sample is subsequently detached from the larger object using a micromanipulator. Exemplary techniques include but are not limited to those disclosed in U.S. Pat. No. 6,188,072, incorporated herein in its entirety by reference.

An additional technique for cutting a completely formed sample and for subsequently detaching the sample is disclosed in U.S. published patent application 2002/0121614, incorporated herein in its entirety by reference, which discloses a method of sample separation and lift-out by cutting with an ion beam a first cut into the wafer at a substantially normal incidence, and subsequently cutting with an ion beam a second cut into the wafer, undercutting the target so that the sample is completely released from the wafer. The sample can be removed from the wafer by affixing a probe to the sample, and then separating the sample from the wafer with the probe. It is to be understood that any of these disclosed methods, as well as others known to the skilled artisan, for forming a sample from a portion of the wafer, and for removing this sample from the wafer may be employed in accord with the present invention.

FIG. 2C illustrates an exemplary method for undercutting the membrane-shaped sample 104. In the embodiment depicted in FIG. 2C, the incident angle of the beam B is shifted to orient the vector B so that it is tilted from the surface 112 in order to form a wedge 126 underneath the rectangular prism. It is noted that either the proximal 120 or distal 122 object cross section surfaces or both surfaces may optionally be polished with a FIB beam after the formation of the substantially parallel trenches 110 and 108.

There are different techniques known in the art for reorienting a corpuscular beam relative to an object upon which the beam is incident. In some embodiments, the object is situated on rotatable and tiltable stage, and an angle of incidence is changed by rotating and/or tilting the stage. In some embodiments, the beam source is an ion beam column, and the angle of incidence is changed by rotating or tilting the beam column. For example, a disclosure of rotation of a corpuscular beam column is available in U.S. Pat. No. 5,329,125, incorporated herein by reference. Nevertheless, this is not limiting, and it is noted that other techniques known in the art for tilting beam column are also appropriate for the present invention.

It is also noted that a combination of known techniques is also appropriate for the present invention.

Figure 2D:
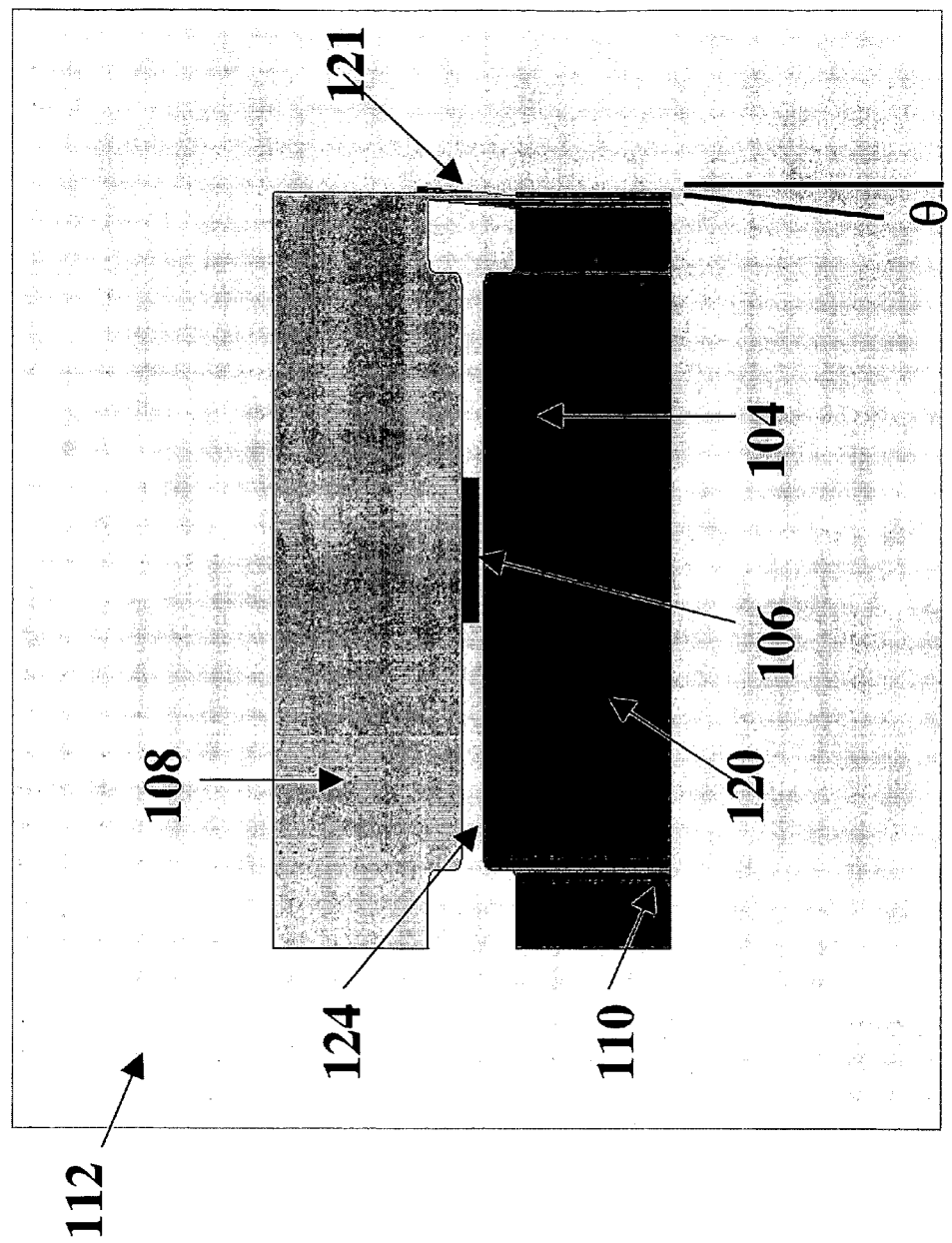
FIG. 2D provides a perspective view of an exemplary embodiment of sample formation.

FIG. 2D provides a perspective view of the next step of sample formation, whereby one 121 of the two remaining walls connecting sample 104 to object 102 is cut away. In the exemplary embodiment of FIG. 2D, the thin connecting wall 121 is cut away using a milling beam. It is noted that according to some embodiments, the thin connecting wall 121 is optionally cut at an angle $\square$ to the X axis. Exemplary values of $\square$ range from about 0.01° to about to 0.2°.

As depicted in embodiments of FIG. 2D, when connecting wall 121 is cut at an angle$\square$, any geometric symmetric between the proximal object cross section surface 120 and the distal object cross section surface 122 is broken.

In particular embodiments, before sample removal, a probe or needle is attached to the sample in order to remove the sample from the wafer. In some embodiments, the object 102 is resting on a stage (not shown), and once the needle or probe is attached to the object 102, the sample is removed by lowering the stage.

It is noted that appropriate needles are available from, for example, The Micromanipulator Co., Inc. (Carson City, Nev.).

Figure 3A:
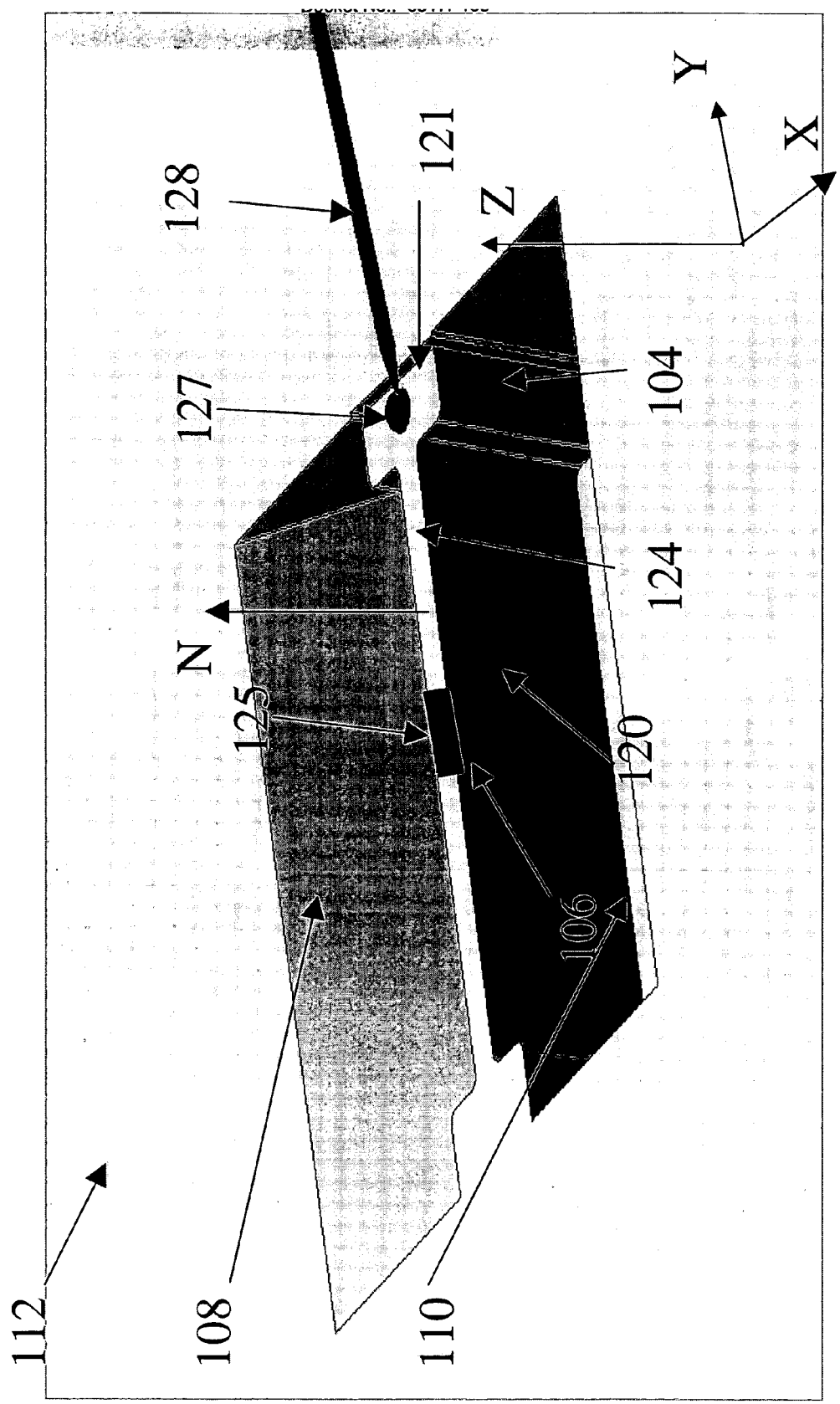
FIG. 3A provides a perspective view of an exemplary embodiment of probe attachment to a sample.

FIG. 3A provides an illustration of an exemplary system wherein a needle 128 is welded to sample 104 using metal deposition with FIB. It is to be understood that welding is just one method of affixing needle 128 to sample 104, and that any other technique, including affixing needle 128 using electrostatic attractive forces or adhesive, is appropriate for the practice of the present invention.

The translational and rotational motion of needle 128 may be controlled by a human operator, or alternatively, may be controlled by a robotic controller.

Figure 3B:
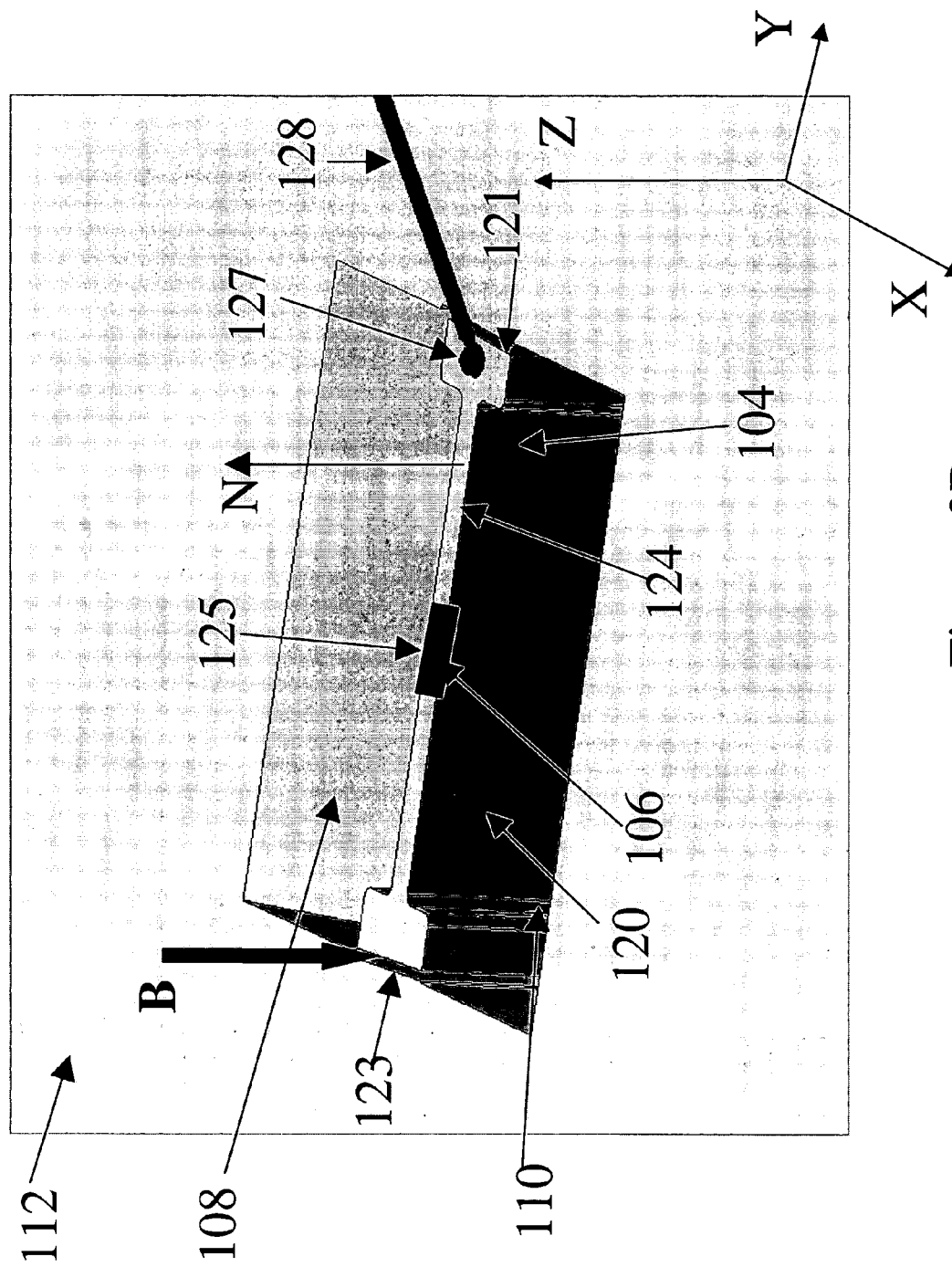
FIG. 3B provides a perspective view of an exemplary embodiment of sample formation.

In specific embodiments, the position of the needle is controlled using a vacuum or atmosphere manipulator. In embodiments in which the methods of the current invention are performed automatically, the motion of the needle is controlled by a robotic controller. Although the needle or probe may be attached to the sample at any angle and to any location on the outer surface 124 of the sample 104, it is now disclosed specific orientations by which the needle or probe is attached to the sample 104. FIGS. 3A and 3B illustrates an exemplary needle orientations and location. Thus, according to some embodiments, the probe or needle is affixed to said outer surface 124 of the sample such that said probe is substantially nonparallel to the outer surface of the sample 124.

In the exemplary embodiment illustrated in FIGS. 3A and FIGS. 3B, it is noted that the probe or needle 128 is oriented away from the outer surface 124. According to some embodiments, this orientation implies that the minimal distance between the center 125 of the outer surface 124 and a vector representing the projection of said probe onto the outer surface is given by the distance between the center 125 of the outer surface 124 and the point of contact 127 between the probe or needle 128 and the outer surface of the sample 124. According to some embodiments, the probe or needle 128 is oriented at an angle that is substantially 55 degrees from the normal vector of the outer surface 124 of the sample 104.

It is noted that in embodiments depicted in FIGS. 3A and 3B, a probe or needle vector originating at the point of contact 127 in the direction of the probe or needle is oriented in the (1,1,1) direction relative to the x-y-z axis affixed to the sample 104. It is noted that the (1,1,1) orientation of the attached needle once more distinguishes between the proximal object cross section surface 120 and the distal object cross section surface 122.

Figure 3C:
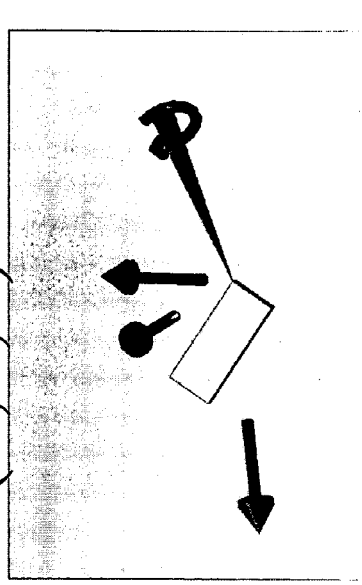
FIG. 3C provides an illustration of various rotation angles with a needle orientation of (1,1,1)
Figure 3C:
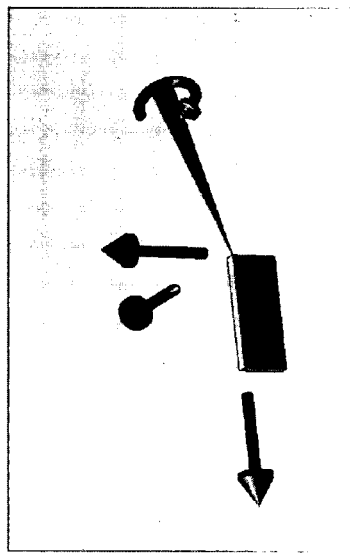
Figure 3C:
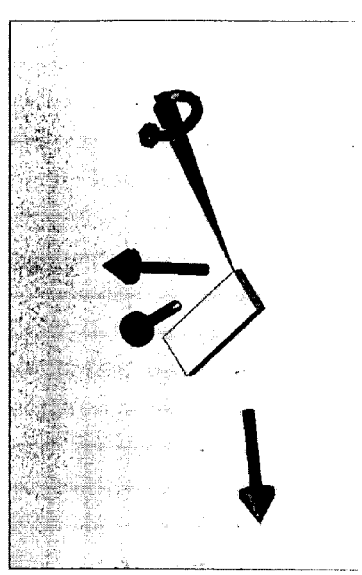
Figure 3C:
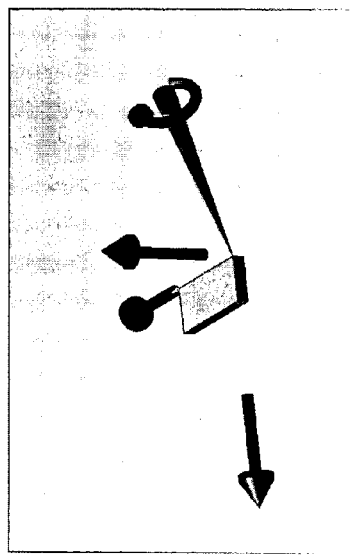

In some embodiments, the probe or needle orientation facilitates rotation of the sample 104 upon removal from the object 102 such that the proximal object cross section surface 120 faces upwards once the sample 104 has been removed from the wafer 102. In some embodiments, the rotation is substantially a 120 degree rotation, as depicted in FIG. 3C.

FIG. 3B illustrates an embodiment of the present invention wherein once the probe or needle is attached, a second wall 123 attaching the sample 104 to the object 102 is cut away. In some embodiments, the cutting of the second wall 123 is performed effected with a focused ion beam.

Once the sample 104 with the probe or needle 128 attached is cut away and detached from the object 102, the sample 104 is removed from object 102. In some embodiments, this removal is effected by lifting the sample 104 from the object with the affixed probe 128. In some embodiments, removal of the sample 104 is effected by lowering a stage (not shown) upon which object 102 is resting while the sample is attached to a needle or probe 128.

Figure 4A:
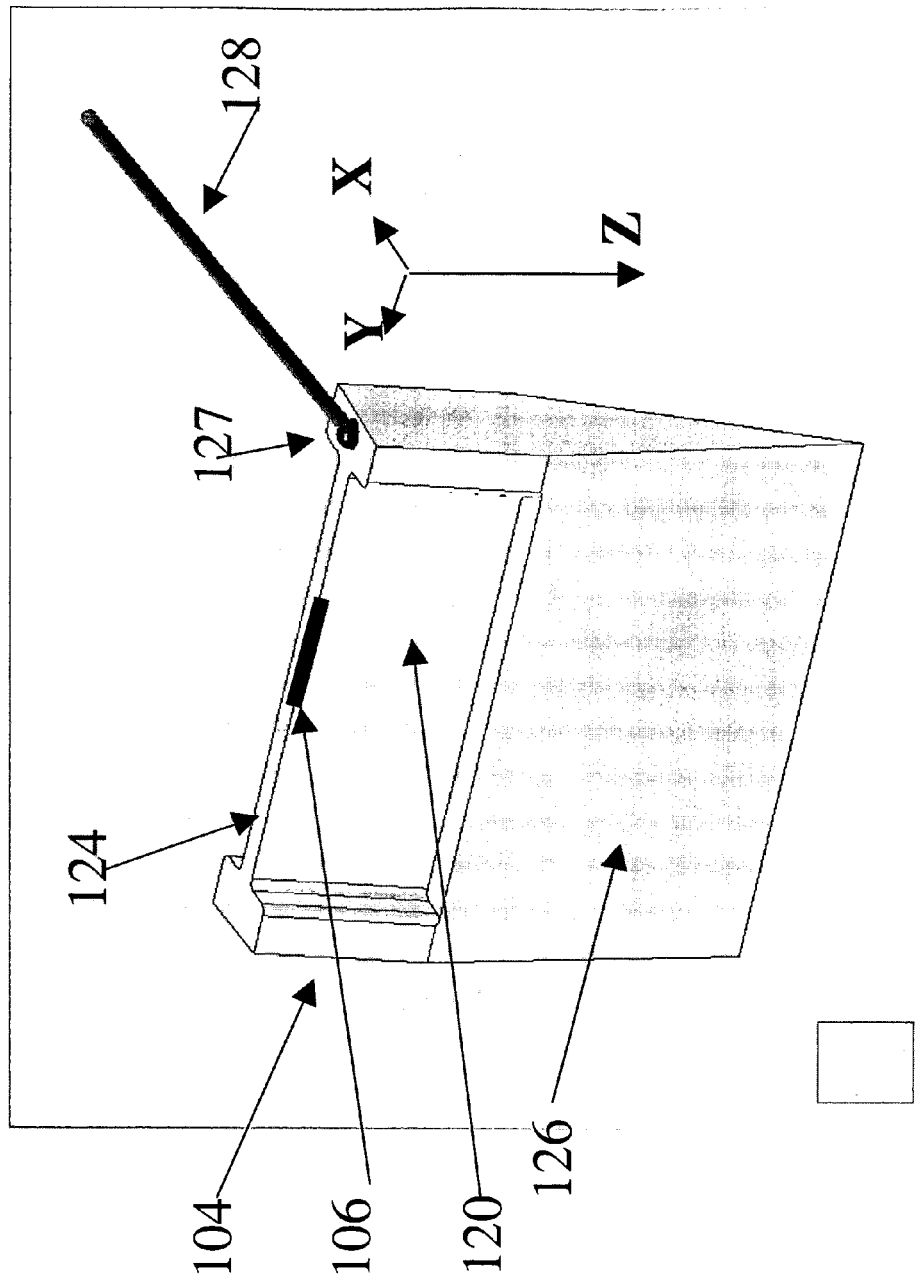
FIG. 4A provides a perspective view of an exemplary sample after being extracted from the wafer.
Figure 4B:
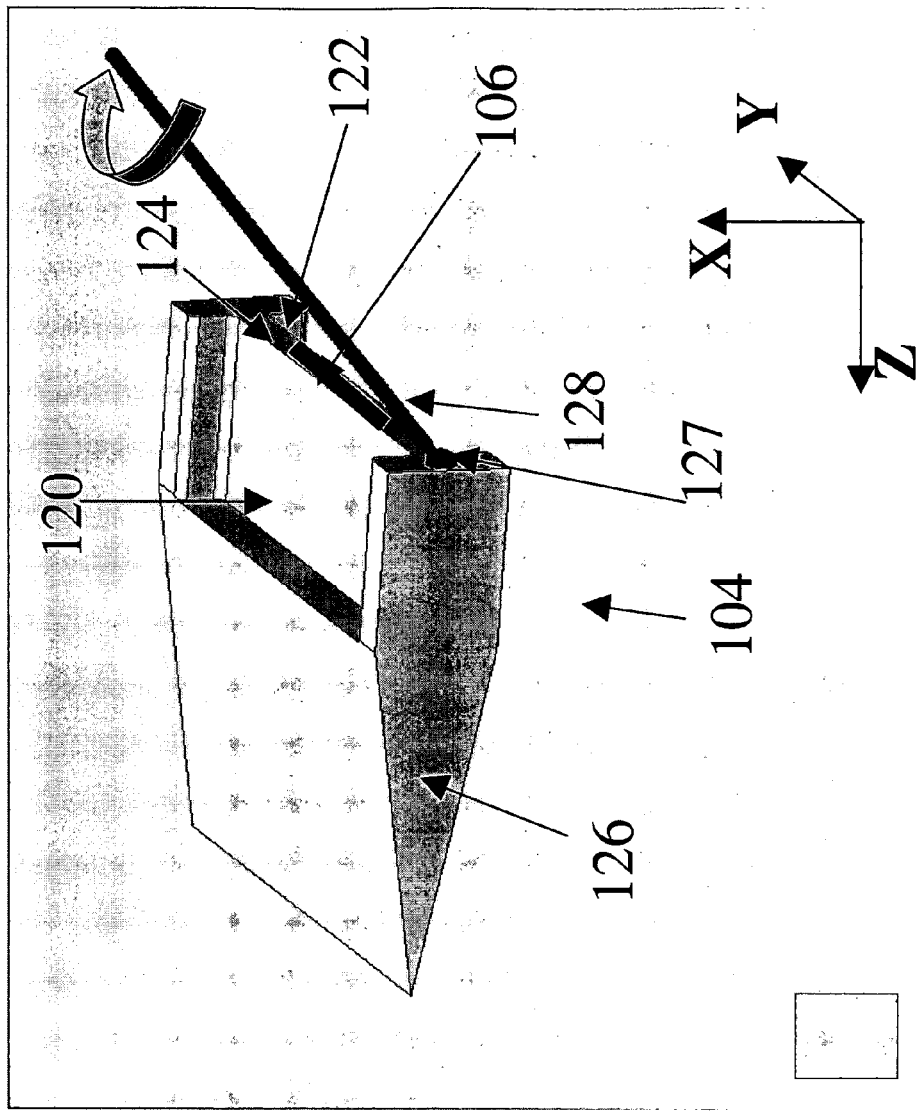
FIG. 4B provides a perspective view of an exemplary sample after being rotated.

An exemplary illustration of sample 104 after sample 104 is extracted from object 102 and rotated is provided in FIGS. 4A and 4B. It is noted that the membrane shaped sample 104 depicted in FIGS. 4A-B has a beam shape in the Y-Z plane. Although the beam shape is not a requirement of the present invention, it is understood that this shape may imbue the sample with extra stability, lowering the probability that the sample will crack or break during sample formation, sample removal or imaging of the sample. It is understood that if the original sample 104 is too thin (in the X direction according to the axis provided in FIG. 4A), then the sample is more likely to be fragile, and could be physically damaged upon removal from the wafer, or thereafter, and could also adversely impact efforts to automate this process. On the other hand, if the original sample 104 is too thick, this may encumber subsequent efforts to thin the sample so as allow electron transparency analysis in the thickness dimension (the X dimension depicted in FIG. 4A), for those embodiments where it is desired to subject the sample to electron transparency analysis. For embodiments in which the sample is subsequently thinned using FIB milling, a sample that is initially too thick concomitantly increases the time necessary to FIB mill the sample to a thickness appropriate for electron transparency analysis.

Figure 5A:
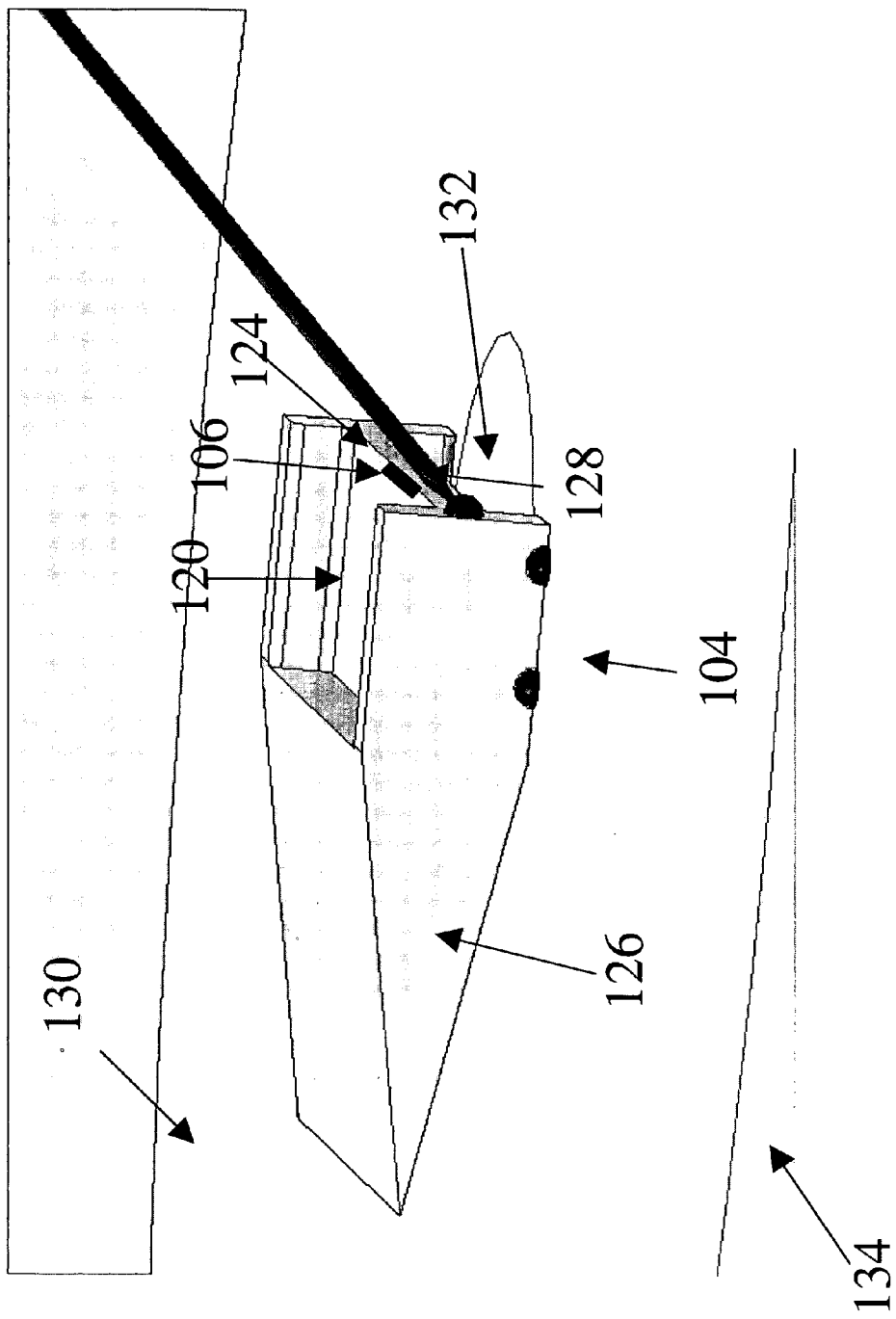
FIG. 5A provides a perspective view of an exemplary sample situated on a sample support.

As illustrated in FIG. 5A, subsequent to the extraction of sample 104 from object 102, sample 104 is affixed to an upper surface 130 of a sample support 134. In some embodiments, the sample 104 is beneath an ion beam when extracted from object 104, attached to probe or needle 128 and suspended in the vacuum chamber. Subsequently, a stage holding a sample support 134 is brought underneath sample 104, so that it may be lowered onto the desired location of the sample support 134.

It is noted that in embodiments depicted in FIG. 5A, sample 104 is affixed to sample support 134 such that the outer surface 124 of the sample 104 is substantially perpendicular to upper surface 130 of sample support 134, thereby allowing the subsequent electron transparency analysis of a cross section of sample 104. In one embodiment, sample 104 is rotated as depicted in FIG. 4B in order to achieve the desired orientation of sample 104 relative to sample support 130.

Optionally, sample 104 is rotated so that an object cross section surface is substantially parallel to the upper surface 130 of sample support 134. In some embodiments, sample 104 is rotated so that proximal object cross section surface 120 is substantially parallel to the upper surface 130 of sample support 134.

According to some embodiments, an object cross section of the sample that is "substantially parallel to the surface of the sample support" is parallel to the surface of the sample support within a tolerance that is at most 10 degrees. In some embodiments, this tolerance is at most 5 degrees. In some embodiments, this tolerance is at most 3 degrees. In some embodiments, this tolerance is at most 1 degree.

In particular embodiments, needle 128 or other appropriate probe is removed after sample 104 is situated on sample support 134.

Sample 104 is then optionally affixed to an appropriate sample support for optional microanalysis. In exemplary embodiments, the microanalysis includes transparency analysis.

Figure 5B:
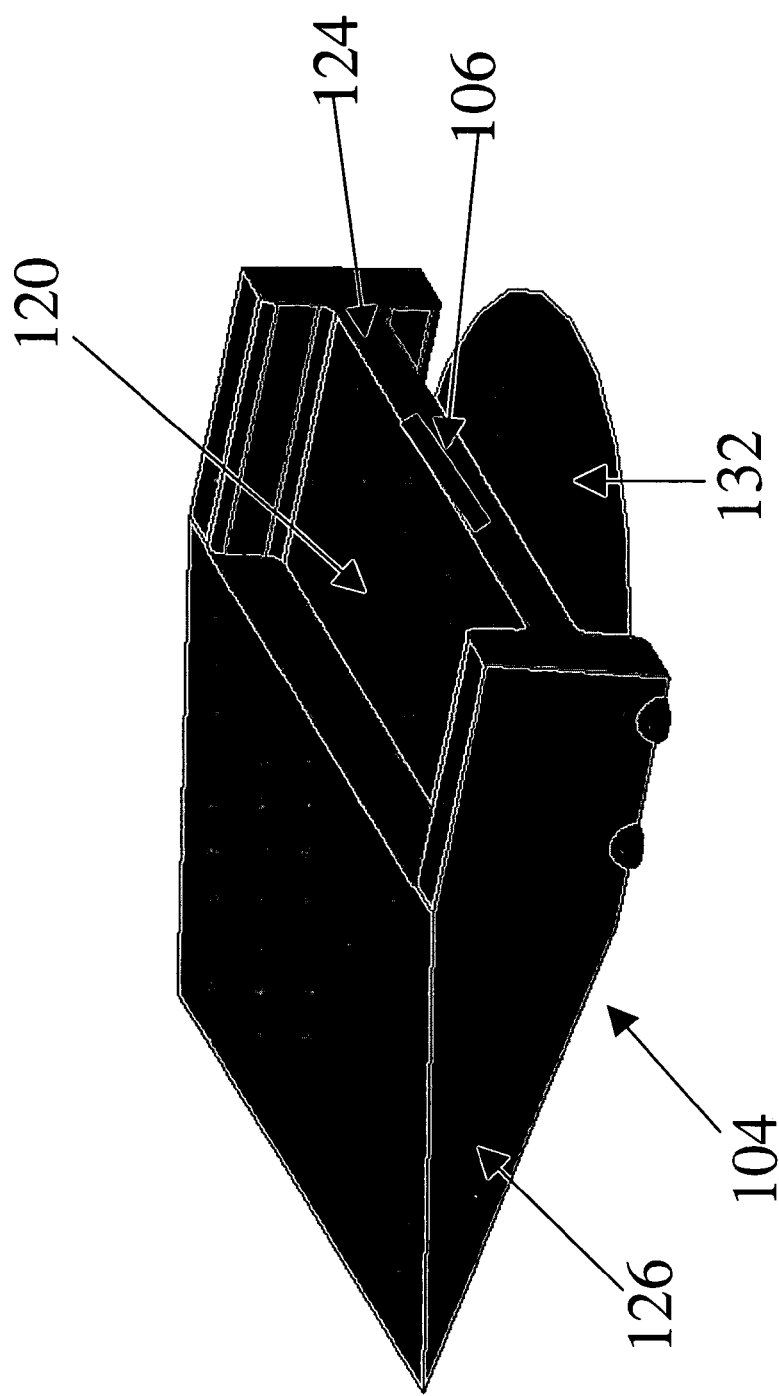
FIG. 5B provides a perspective view of an exemplary sample situated on an exemplary sample support after the probe is detached from the sample.

As illustrated in FIGS. 5A and 5B, sample support 134 includes at least one optional aperture 132, through which an electron beam can pass during electron transparency analysis. In specific embodiments, sample 104 is positioned on upper surface 130 of sample support 134 such that at least part of sample 104 is on or over one of apertures 132. In other embodiments, the sample support is solid, and lacks an aperture.

In particular embodiments, the sample 104 is subjected to electron transparency analysis while mounted on the sample support 134. Thus, sample 104 is positioned on upper surface 130 of sample support 134 such that at least part of sample 104 is on or over one of apertures 132 allows for an electron beam to traverse both at least a portion of the sample 104 and an aperture 132.

Figure 5C:
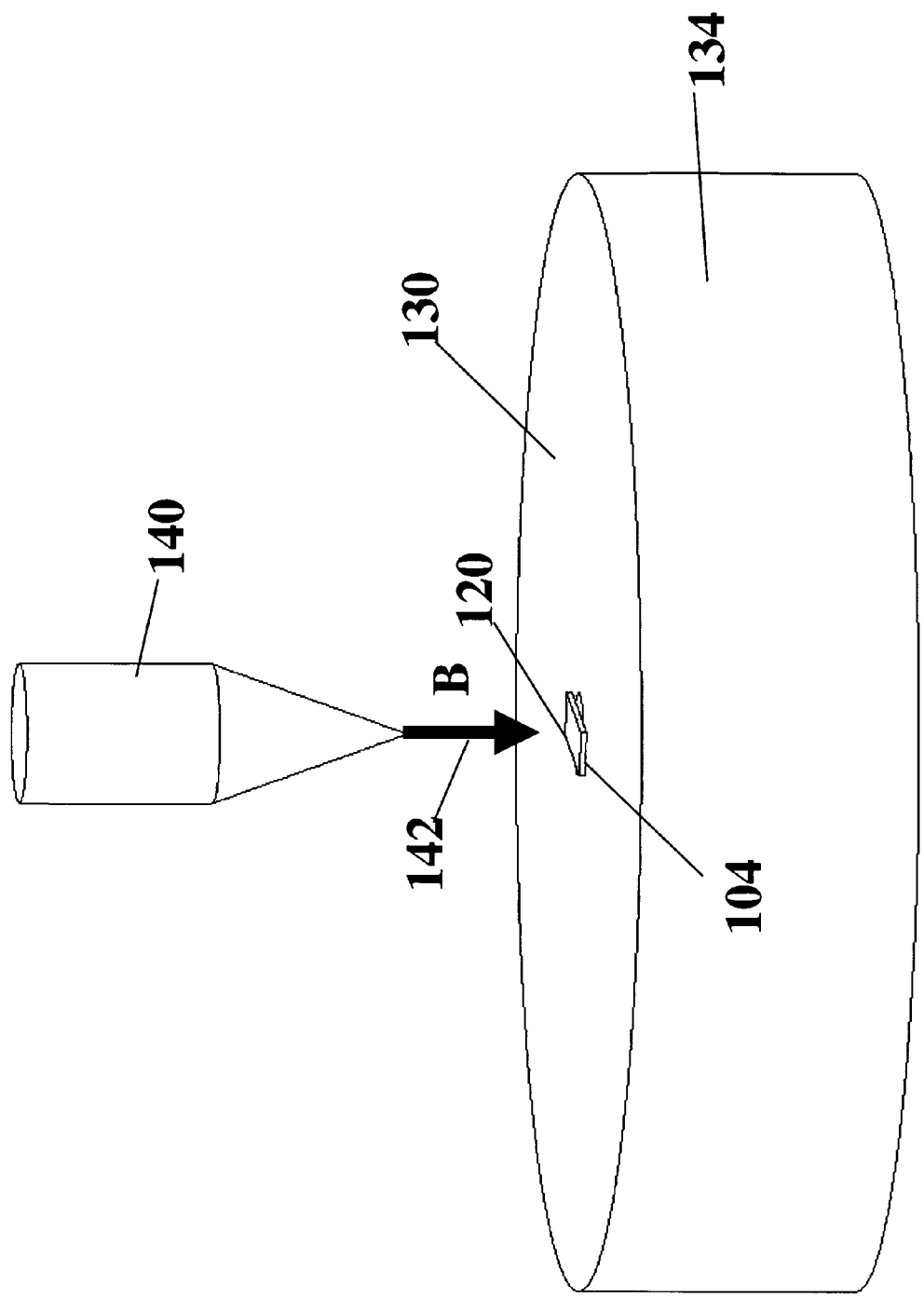
FIG. 5C provides an isometric illustrated view of an exemplary sample subjected to a particle beam while situated on an exemplary sample support.

As illustrated in FIG. 5C, subsequent to mounting on the sample support 134, the sample 104 is subjected to a particle beam 142 such as an electron beam or an ion beam such as a focused ion beam emitted from beam source 140. As illustrated in FIG. 5C, the electron beam is incident substantially normally to an object cross section surface of the sample 104 such as the proximal 120 or distal 122 object cross section surfaces. As illustrated in FIG. 5C, the electron beam is collinear with a line that is substantially perpendicular to the upper surface 130 of sample support 134.

According to some embodiments, an electron beam that is "incident substantially normally" to a surface of a sample in the context of electron transparency analysis is incident normally to the local plane of the surface within a tolerance that is at most 5 degrees. In some embodiments, this tolerance is at most 3 degrees. In some embodiments, this tolerance is at most 1 degrees. In some embodiments, this tolerance is at most 0.5 degree.

According to some embodiments, an electron beam that is "incident substantially normally" to a surface of a sample in the context of surface analysis is incident normally to the local plane of the surface within a tolerance that is at most 10 degrees. In some embodiments, this tolerance is at most 5 degrees. In some embodiments, this tolerance is at most 3 degrees. In some embodiments, this tolerance is at most 1 degree.

According to some embodiments, a focused ion beam that is "incident substantially normally" on a surface of a sample or object in the context of sample formation or thinning is incident normally to the local plane of the surface within a tolerance that is at most 10 degree. In some embodiments, this tolerance is at most 5 degrees. In some embodiments, this tolerance is at most 3 degrees.

Sample support 134 includes at least one such aperture 132, and in particular embodiments, sample support 134 includes many such apertures 132, so that more than one sample 104 may be affixed to the sample support 134, with each sample 104 affixed such that part of the sample 104 is on or over an aperture 132. An example of an embodiment in which more than one sample 104 is affixed to the sample support 134 is provided in FIG. 6.

In some exemplary embodiments, a density of samples mounted on a sample support is on the order of magnitude of 100 samples per square millimeter. Not wishing to be bound by theory, it is noted that in some embodiments the mounting of a plurality of samples onto the sample supports facilitates a process whereby a single sample support is reused for different sample without a need to remove the sample support from the tool.

Figure 6:
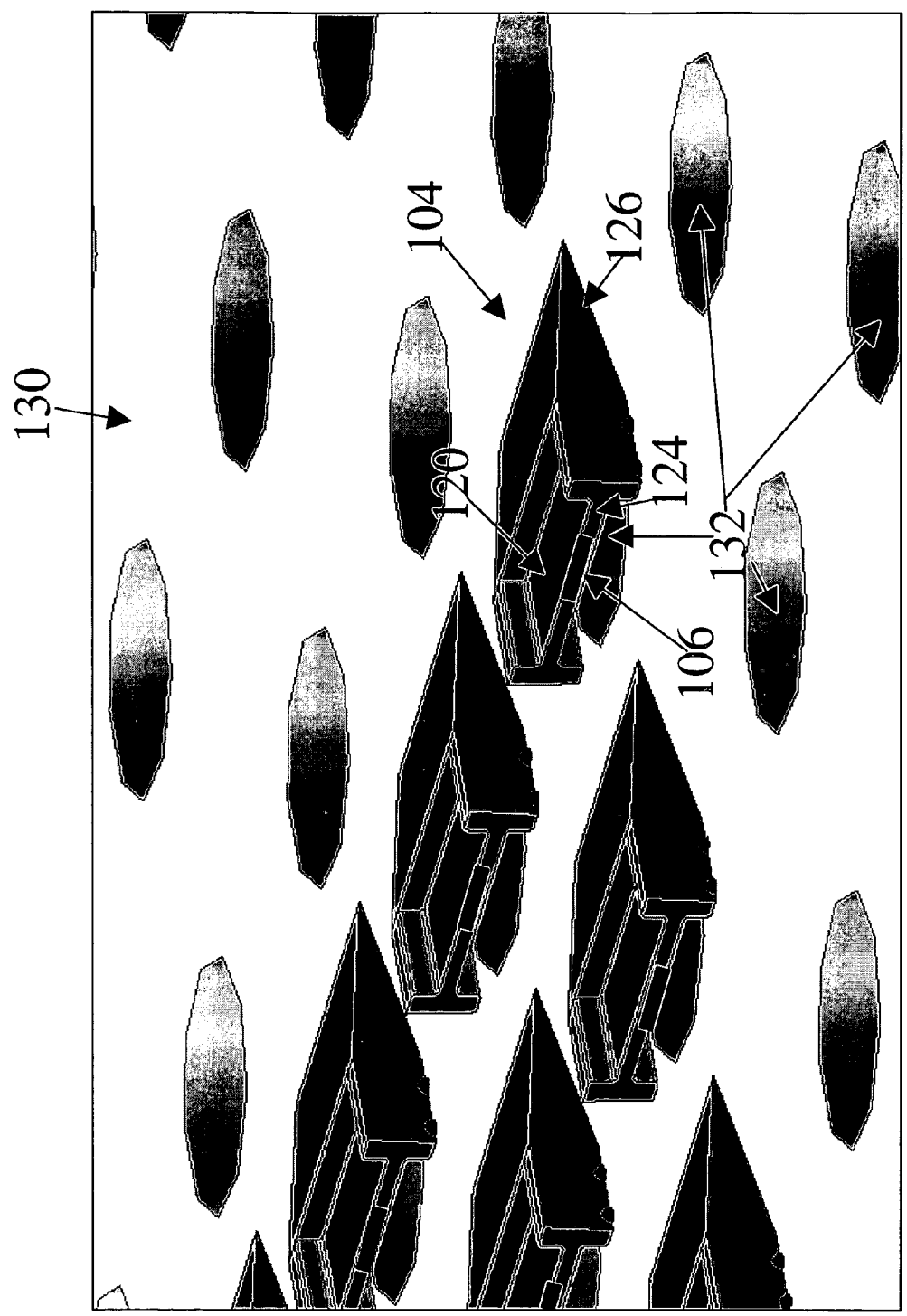
FIG. 6 provides a perspective view of an exemplary embodiment in which more than one sample situated on the sample support.

It is noted that in the embodiment of FIG. 6, only a minority of the surface area of sample support 134 is occupied by the apertures 132. This should not be construed as a limitation of the present invention. Any sample support comprising solid surface and at least one aperture is appropriate for the present invention. Other exemplary sample supports include a TEM grid, well known in the art, in which an overwhelming majority of surface area of the sample support is occupied by apertures. Nevertheless, it is recognized that it is generally easier to automate the process of situating the sample on the surface of a solid support if the apertures occupy less than the overwhelming majority of the surface area of sample support.

It is noted that the images of the mounting of the sample 104 onto the sample support 134 as provided in FIGS. 5-6 only illustrates certain embodiments of the invention. Alternately, the sample 104 is mounted onto the sample support 134 in geometric orientations other than the previously illustrated orientation wherein object cross section surface is substantially parallel to the upper surface 130 of sample support 134.

Figure 7A:
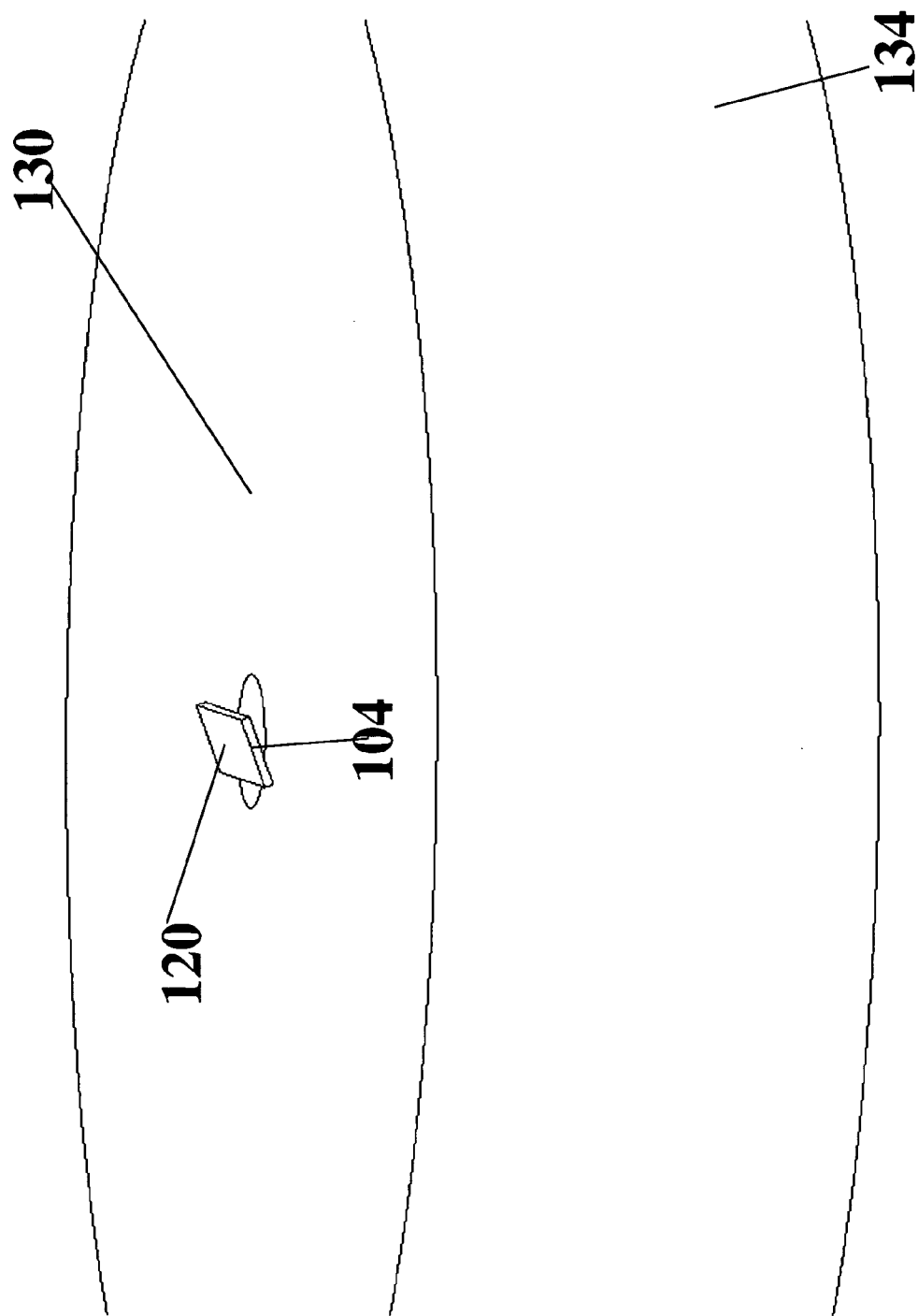
FIGS. 7A-B provides isometric illustrated view of an exemplary sample situated on exemplary sample supports.
Figure 7B:
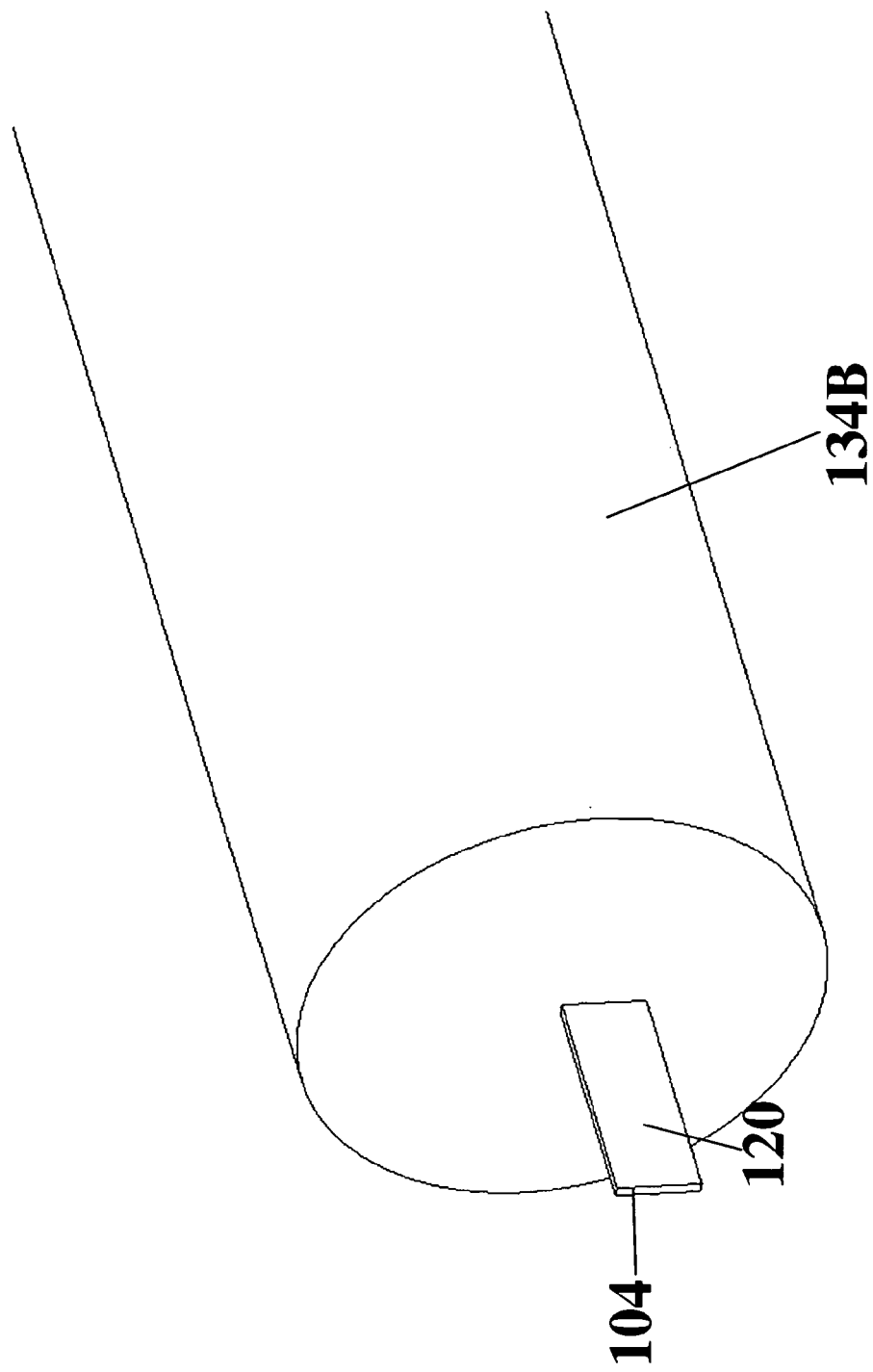
Figure 7C:
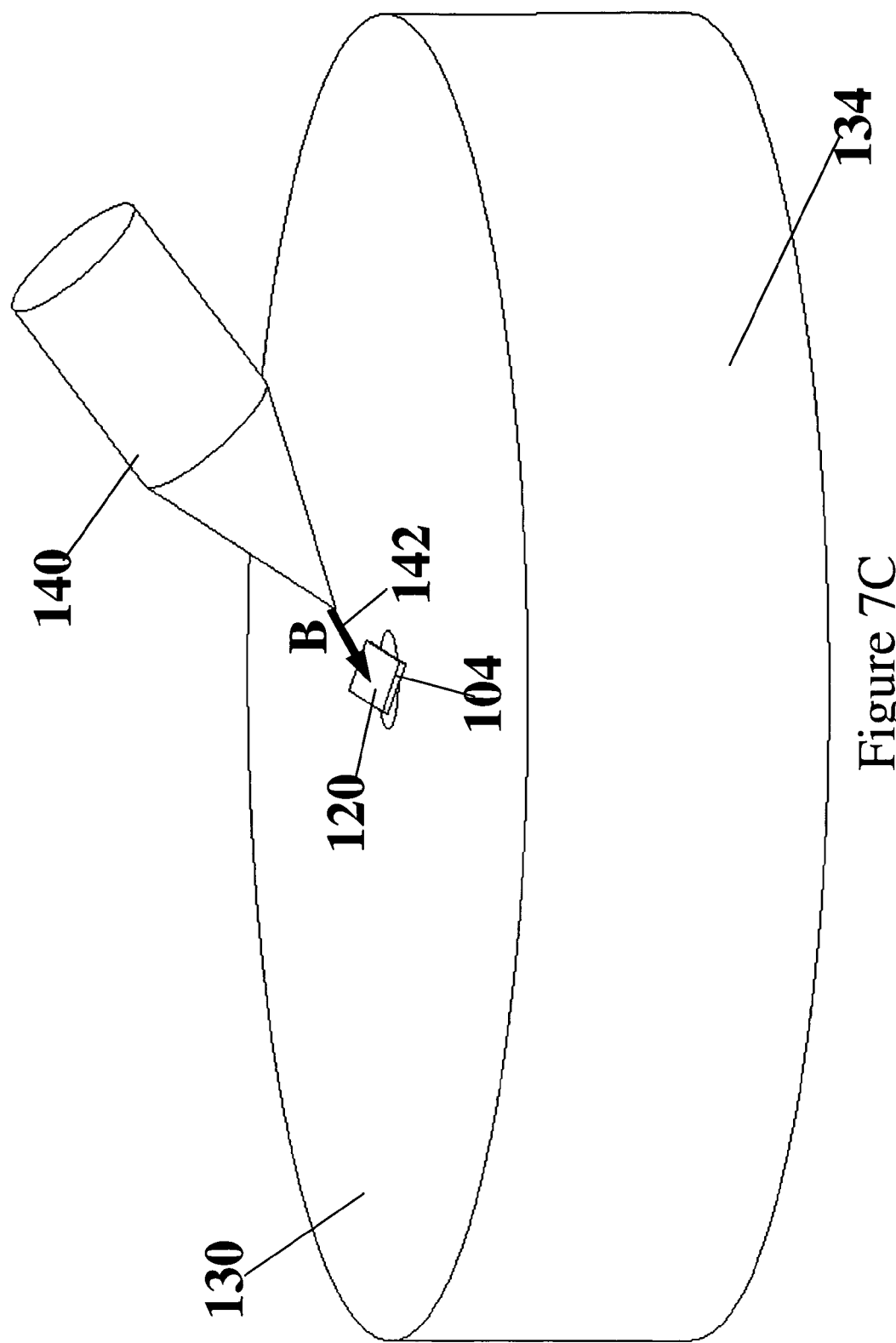
FIG. 7C provides isometric illustrated views of an exemplary sample subjected to a particle beam while situated on an exemplary sample support.

FIGS. 7A and 7B provide an illustration of sample 104 mounted onto the sample support 134 according to certain embodiments of the present invention. As illustrated in FIG. 7C, subsequent to mounting on the sample support 134, the sample 104 is subjected to a particle beam 142 such as an electron beam or an ion beam such as a focused ion beam emitted from beam source 140. As illustrated in FIG. 7C, the electron beam is incident substantially normally to an object cross section surface of the sample 104 such as the proximal 120 or distal 122 object cross section surfaces. As illustrated in FIG. 7C, the electron beam is collinear with a line that is oblique to the upper surface 130 of sample support 134.

In certain embodiments it is desired to subject at least a portion of the sample to electron transparency analysis. In particular embodiments, when the membrane shaped sample 104 affixed to sample support 134 is too thick for electron transparency analysis, where the thickness is the distance between the proximal object cross section surface 120 and the distal object cross section surface 122, sample 104 is milled to an appropriate thickness while affixed to sample support 134, preferably using an ion bean milling device.

In yet other embodiments, the appropriate sample thickness may not be known a priori, and may need to be determined in situ while the membrane shaped sample 104 is affixed to sample support 134.

It is now disclosed for the first time an automatic tool for forming, extracting and imaging a sample of an object including an electron microscopy device for imaging the sample such that at least a portion of an electron beam traverses at least a portion of the sample. It is noted there is an ongoing need for tools including both an ion beam milling device and an electron transparency microscopy device, especially in the field of semiconductor manufacturing where there is a need for tools useful for defect analysis and process control.

In some embodiments, the device includes one or more stages for supporting the object and optionally the obtained sample. In some embodiments wherein an obtained sample is supported on a stage, the electron beam source and electron detector are situated on opposite sites of the upper surface of at least one stage. In some embodiments, this geometric configuration provides for detection of electrons that pass through a sample situated on a stage. Alternately, the device includes a stage for supporting the object and the device does not include a stage for supporting the sample.

Exemplary objects from which a sample is extracted in the device include but are not limited to semiconductor wafers. In some embodiments, at least one stage is adapted to support a silicon wafer. In some embodiments, at least one stage includes a support surface for supporting the object, wherein the support surface has a size of at least 30,000 mm$^2$, and is large enough to support a 200 mm wafer or larger In particular embodiments wherein a sample is not supported on a stage, the sample is imaged using electron transparency analysis when attached to and supported by a needle or probe. In these embodiments, the electron beam source and electron detector are situated so that they are on opposite sides of an area in which the sample is to be located while subjected to electron transparency analysis.

In particular embodiments, the tool also includes a robotic manipulator including a needle or probe for removing a sample formed with an ion beam from the object. Optionally, the robotic manipulator is programmed to situate the obtained sample on an electron microscopy sample support for microscopy analysis.

FIGS. 8A-E provide isometric illustrated views and isometric broken illustrated views of apparatus according to some embodiments of the present invention of a first multicolumn tool 322 including a movable stage, a FIB device, a sample manipulation device, and an electron microscopy device for electron transparency analysis. Referring now to FIGS. 8A-E, it is seen that the first multicolumn tool 322 includes a FIB Column 310 for forming a sample from a larger object such as a wafer or die, an electron beam source 308 for subjecting the sample to an electron beam such that at least a portion of the electron beam traverses the sample, an electron detector 306 for detecting electrons derived from the portion of the electron beam that traverses, at least one stage 312, and a robotic manipulator 320 for extracting and manipulating the formed sample. In exemplary embodiments, at least one stage 312, the FIB Column 310, electron beam source 308, electron detector 306, and robotic sample manipulator 320 are located partially or in their entirety within a vacuum chamber 304 for housing the components.

In some embodiments, the stage is translatable in up to three dimensions, and includes a rotation axis (not shown). Optionally the stage 312 includes a tilting axis, for tilting a wafer situated on the stage 312.

Figure 8A:
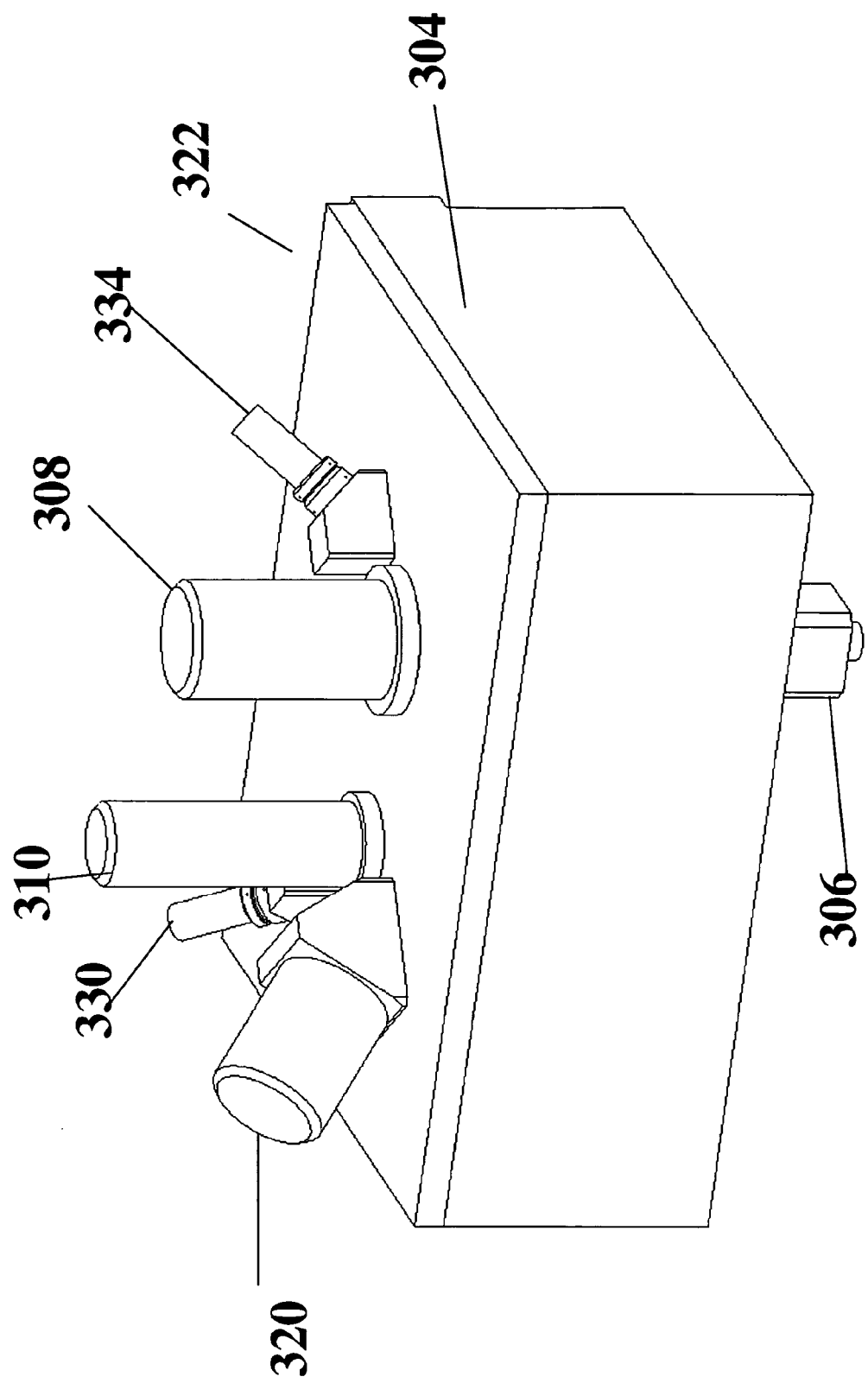
FIG. 8A provides an isometric illustrated views of a tool for sample formation and electron transparency analysis of the formed samples according to some embodiments of the present invention.
Figure 8B:
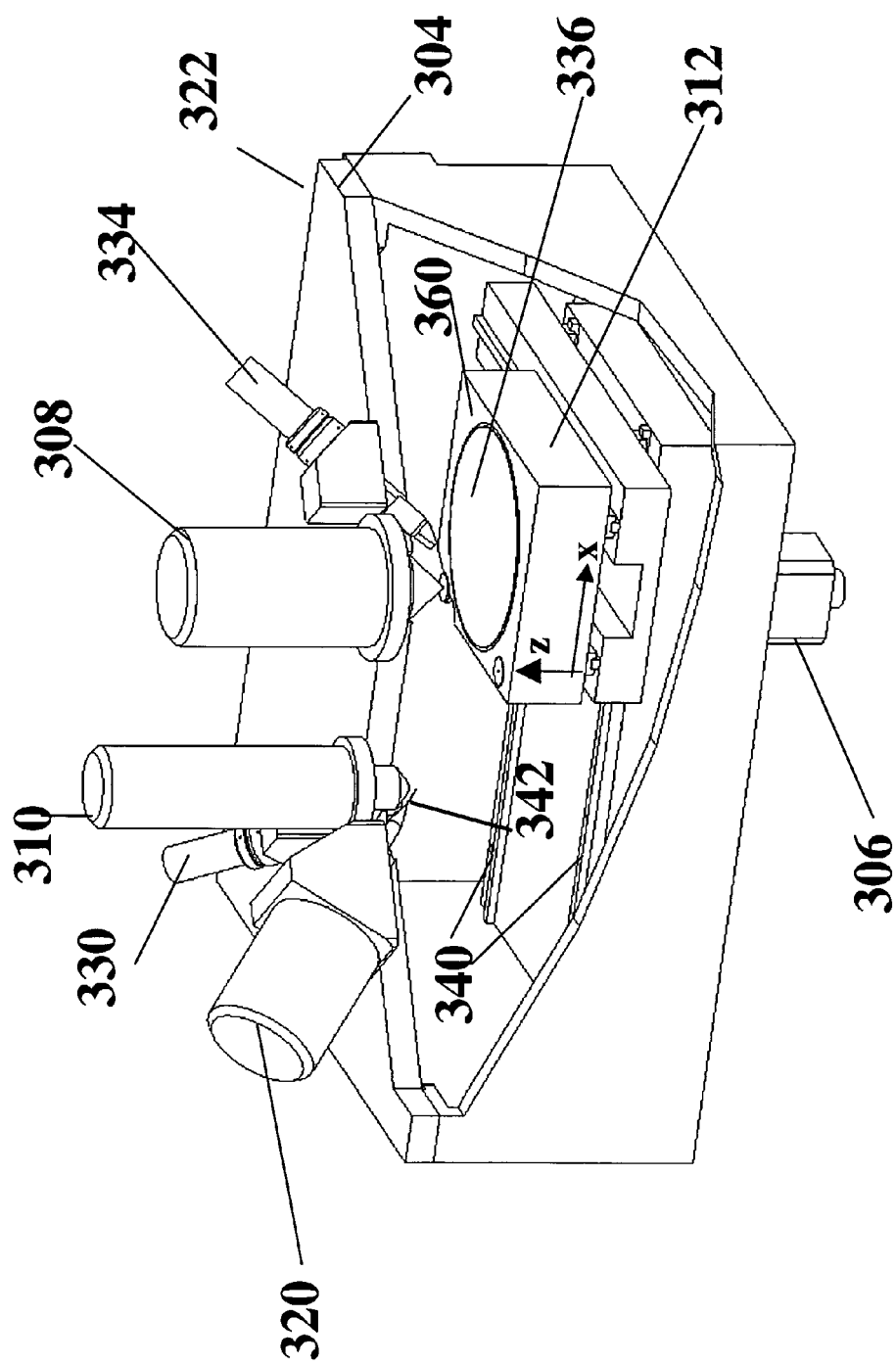
Figure 8C:
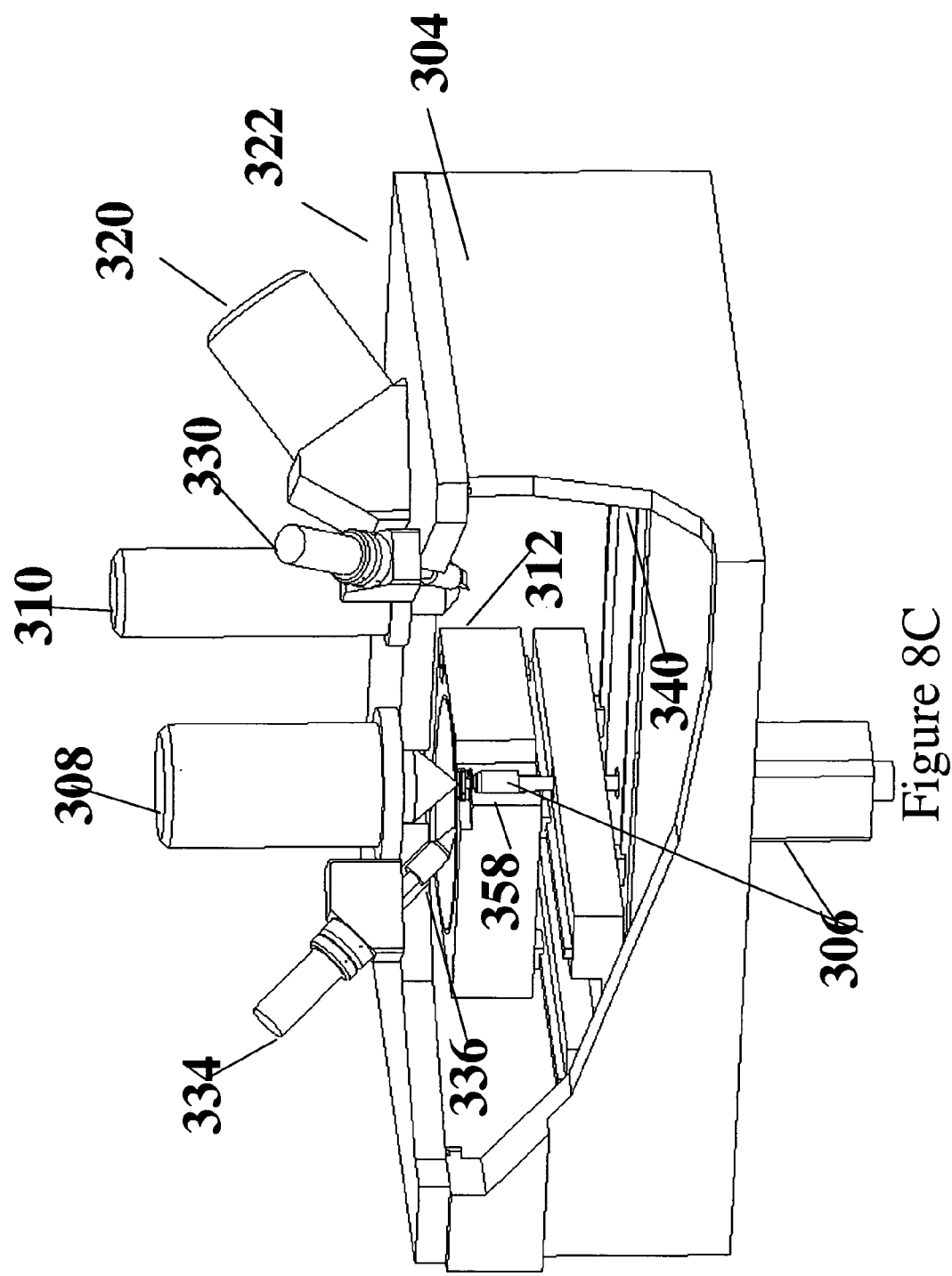

In particular embodiments, an object is placed on a stage 312, which as depicted in FIGS. 8C-8D, includes an optional orifice 358. Optionally, part of the electron detector 306 protrudes through orifice 358.

Figure 8E:
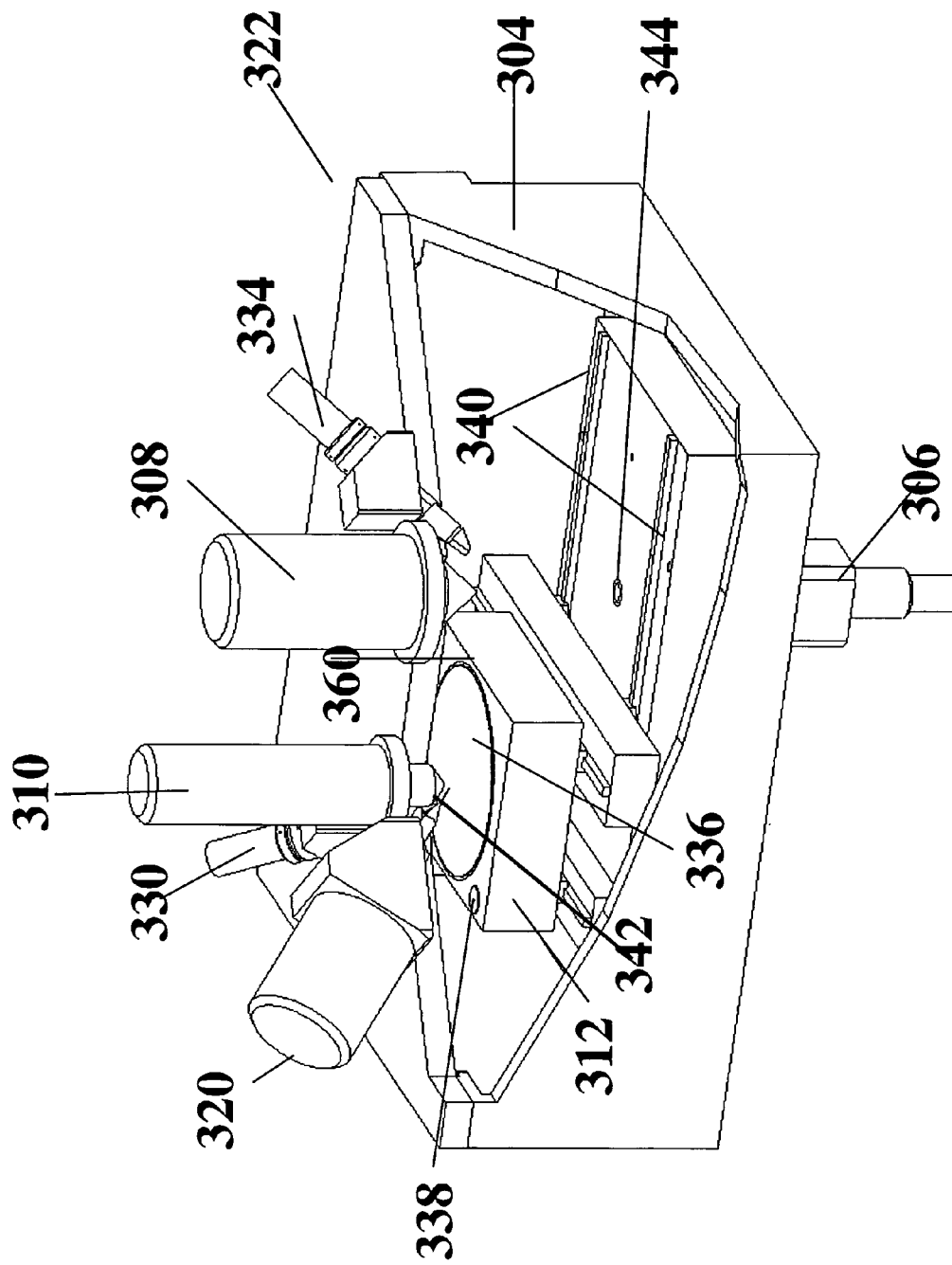

The stage 312 is optionally movable, in particular translatable and rotatable. In some embodiments, the stage is operatively connected to a motor. As illustrated in FIGS. 8B, 8C and 8E the movable stage is mounted on a track 340. In some embodiments, the stage 312 and sample support carrier 350 are also used for supporting a sample optionally situated on a sample support while the sample is subjected to electron transparency analysis. As depicted in FIG. 8, the sample support carrier 350 is located within an orifice 358 in stage 312.

In some embodiments, the stage 312 includes an upper surface or support surface 360 configured to support a 200 mm or larger wafer 336.

In some embodiments, the stage 312 includes an upper surface or support surface 360 with a surface area of at least 30,000 square millimeters.

Optionally, the FIB column 310 and/or the electron beam column 308 can be tilted relative to the stage 312.

It will be appreciated that a second stage other than stage 312 (not shown) is also appropriate for the task of supporting a sample while the sample is subjected to electron transparency analysis. Optionally, the second stage is can be tilted.

The second stage for the sample support can be a manipulator, completely or partially inside the vacuum.

As illustrated in FIG. 8D, the device includes an optional holder 338 for a plurality of sample supports.

As illustrated in FIGS. 8B, 8E the sample manipulator 320 includes a needle or probe 342.

As illustrated in FIGS. 8A-8E, the device includes an optional FIB detector 330 such as an ion detector or electron detector.

As illustrated in FIGS. 8A-8E, a single electron beam source 308 emits electrons, which are detected by an electron transparency detector 306 and an optional backscattered and/or secondary electron detector 334 such as an SEM detector. Nevertheless, it will be appreciated that in some embodiments, there is more than one electron beam source 308. In some embodiments, the electron beam source 308 is an SEM column. In some embodiments, electron beam source 308 is an SEM column, and optionally plays a role in cutting the sample.

As illustrated in FIGS. 8A-E, the electron beam source 308 and an electron transparency detector 306 are situated on opposite sides of sample to be imaged. As illustrated in FIG. 8D, the electron beam source 308 and an electron transparency detector 306 are situated on opposite sides of sample support carrier 350 supporting sample supports for holding the mounted samples, and also on opposite sides of the upper surface 360 of the stage 312.

In contrast, as evident from FIG. 8E, the optional SEM detector 334 is on the same side of the stage 312 as the electron beam source 308.

Although this is appropriate for embodiments as shown in FIGS. 8A-E, this geometry is not a limitation of the present invention, particularly for embodiments wherein the sample is subjected electron transparency analysis while being supported by an attached probe or needle rather than a stage. It will be appreciated that for these embodiments, it is necessary during the time of electron transparency analysis for the electron beam source 308 and electron detector 306 to be situated on opposite sites of the location wherein the analyzed sample is located so that the electron beam provided by the electron beam source 308 can traverse at least a portion of the sample to be detected by the electron detector 306.

It will be appreciated that in some embodiments, the device includes more than one backscattered and/or secondary electron detector 334 and/or more than one electron transparency detector 306. In some embodiments, the device includes an optional optical microscopy device (not shown). In some embodiments, the device includes an optional photon detector (not shown), optionally configured to detect X-rays.

In some embodiments, the electron beam source 308 is an SEM column, and the electron transparency detector 306 is an STEM detector. In other embodiments, the electron transparency detector 306 is a TEM detector.

As illustrated in FIG. 8E, the stage 312 is in the FIB cutting zone. In some embodiments, the electron transparency detector 306 is retractable, and as illustrated in FIG. 8E, the electron transparency detector 306 is retracted prior to moving the stage to the FIB cutting zone.

In particular embodiments, the first multicolumn tool 322 also includes a controller (not shown) including a processor and a memory operatively coupled to at least one device selected from the group consisting of the ion beam source 310, the electron beam source 308, electron detector 306, movable stage 312, second microscopy device (not shown), and the robotic manipulator 320. In a particular embodiments, the controller (not shown) is operatively coupled to the ion beam source 310, the electron beam source 308, and the robotic manipulator 320. In particular embodiments, the controller (not shown) is operative to control any other microanalysis device optionally included in the device.

In some embodiments, the process controller is operative to control the translation and/or rotation of at least one stage such as movable stage 312.

In some embodiments, the first multicolumn tool 322 further includes an optional auger electron detector (not shown) and/or x-ray detector (not shown) for EDX analysis.

In some embodiments, the process controller is programmed so that the tool executes the methods for sample formation, sample rotation, situating of sample onto a sample support, and sample microanalysis disclosed herein.

Figure 9A:
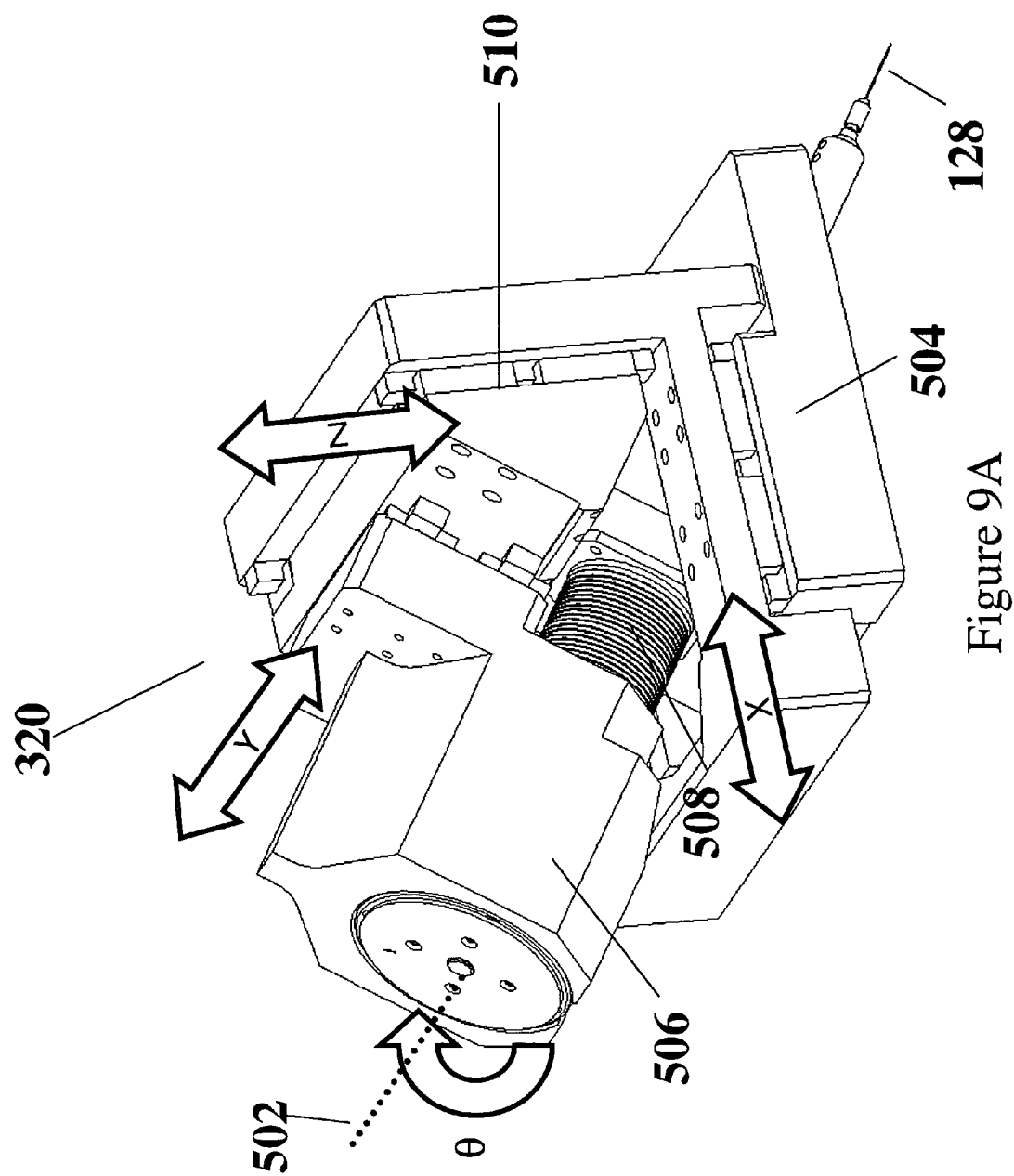
FIGS. 9A-9C provide illustrations of an X-Y-Z-Θ) robotic sample manipulator according to certain embodiments of the present invention.
Figure 9B:
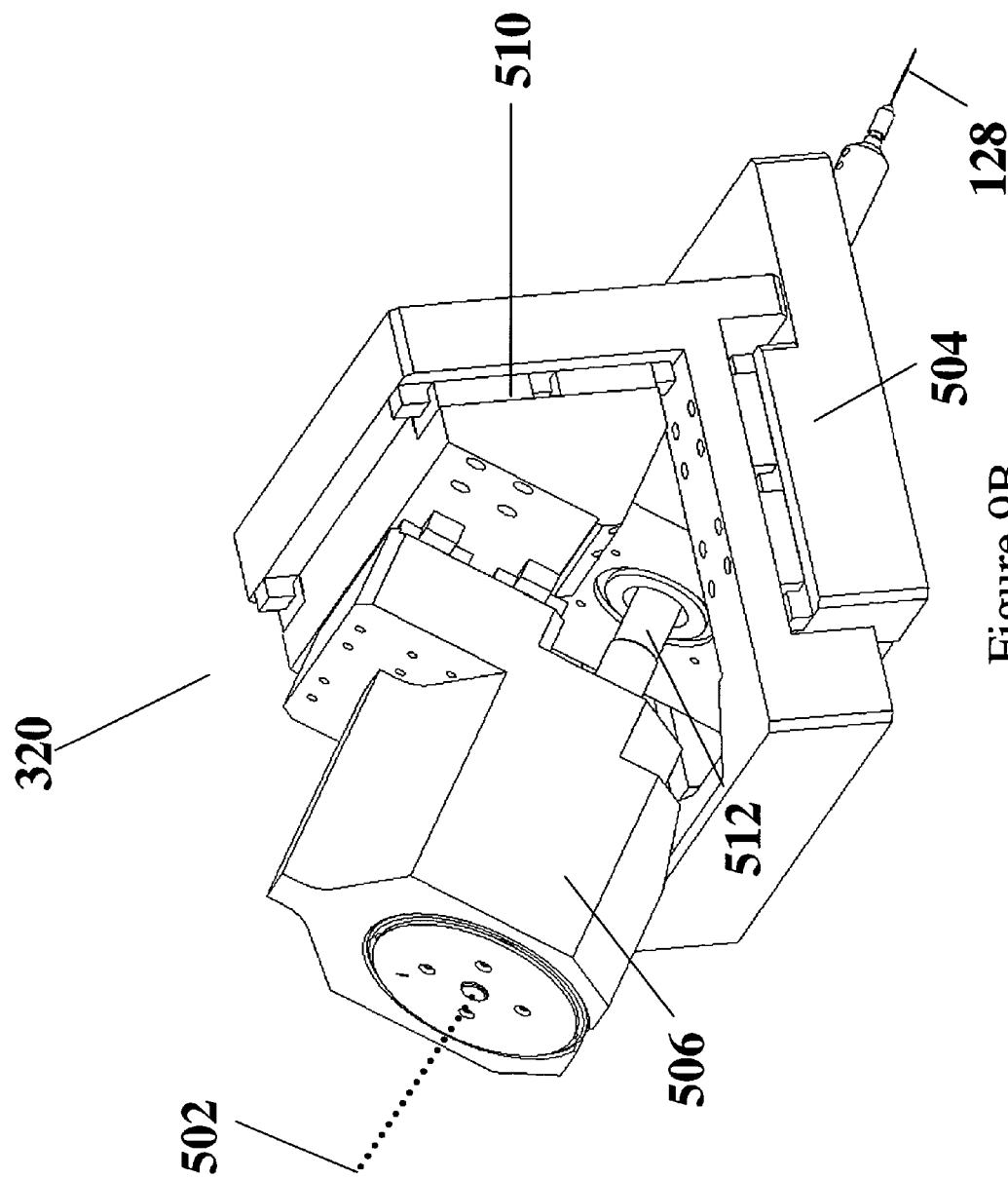
Figure 9C:
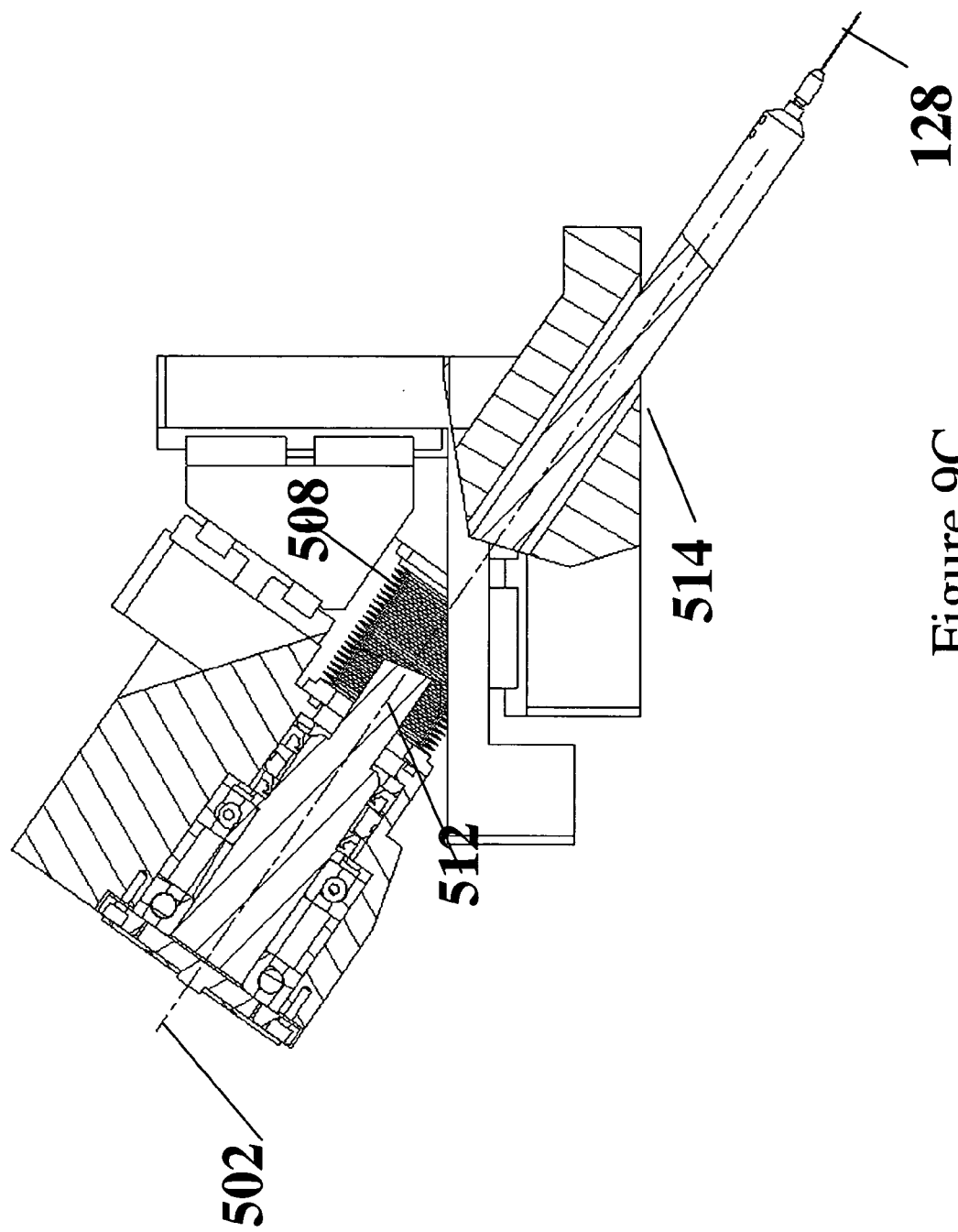

FIGS. 9A-9C provide illustrations of an exemplary X-Y-Z-Θ robotic sample manipulator 320 according to certain embodiments of the present invention. Although the robotic manipulator 320 as disclosed in FIGS. 9A-9C is appropriate for multicolumn tools 322 and 362 described in FIGS. 8A-8E and 10A-10F, it should be appreciated that the robotic manipulator 320 illustrated in FIGS. 9A-9C is provided as an example, and should not be construed as limiting.

It is noted that there is no connection between tool axes illustrated in FIGS. 9A-9C and axes affixed within the object and/or extracted sample described earlier. Furthermore, it is understood that modification can be made to the robotic sample manipulator illustrated in FIGS. 9A-9C, and thus there figures are intended to be illustrative rather than limiting.

As illustrated in FIGS. 9A-9C, the robotic sample manipulator includes a rotation shaft 512 within a flexible bellow 508 situated on a rotation axis 502. The flexible bellow 508 allows for axial and lateral movement of the rotation shaft, while maintaining vacuum sealing. The rotation mechanism includes rotation bearings and seals.

At the end of the rotation axis is a needle or probe 128. In some embodiments, the needle can be used to extract a formed sample from an object.

As illustrated in FIGS. 9A-9B, the rotation axis 502 is oriented substantially 55 degrees from a normal to the manipulator base 504.

FIG. 9C provides a cross section view of the X-Y-Z-Θ robotic sample manipulator. The sample manipulator includes a vacuum sealing surface 514.

FIGS. 10A-10F provide isometric illustrated views and isometric broken illustrated views of a second multicolumn tool 362 for extracting a sample of an object and subjecting the sample to surface analysis according to some embodiments of the present invention.

Referring now to FIGS. 10A-F, it is seen that the second multicolumn tool 362 includes a FIB Column 310 for forming a sample from a larger object such as a wafer or die, an electron beam source 308B for scattering an electron beam off of a surface of the sample, at least one stage 312B, and a robotic manipulator 320 for extracting and manipulating the formed sample, an EDX device 364, and an auger electron detector 366, all located partially or in their entirety within a vacuum chamber 304 for housing the components. Although exemplary the multicolumn tool 362 as depicted in FIGS. 10A-F includes both the EDX 364 as well as the auger electron detector 366, it will be appreciated that certain embodiments of the present invention provide a multicolumn tool with only one of the EDX 364 and the auger electron detector 366.

In some embodiments, the stage 312B is translatable in up to three dimensions, and includes a rotation axis (not shown). Furthermore, the stage 312 includes a tilting axis, for tilting an object or sample situated on the stage 312B.

In particular embodiments, an object is placed on a stage 312B, which is optionally movable, in particular translatable and rotatable. In some embodiments, the stage is operatively connected to a motor. As illustrated in FIGS. 10B-F, the movable stage is mounted on a track 340. In some embodiments, the stage 312B includes a support surface 360 configured to support a 200 mm or larger wafer 336.

In some embodiments, the stage 312 includes a support surface 360 with a surface area of at least 30,000 square millimeters.

Optionally, the FIB column 310 and/or the electron beam column 308 can be tilted relative to the stage 312.

It will be appreciated that a second stage other than stage 312B (not shown) for supporting the object or wafer is also appropriate for the task of supporting a sample while the sample is subjected to surface microanalysis. The second stage for the sample support can be a manipulator, completely or partially inside the vacuum.

As illustrated in FIGS. 10C-F, the device includes an optional holder 338 for a plurality of sample supports.

As illustrated in FIGS. 10B-E the robotic sample manipulator 320 includes a needle or probe 342.

Figure 10A:
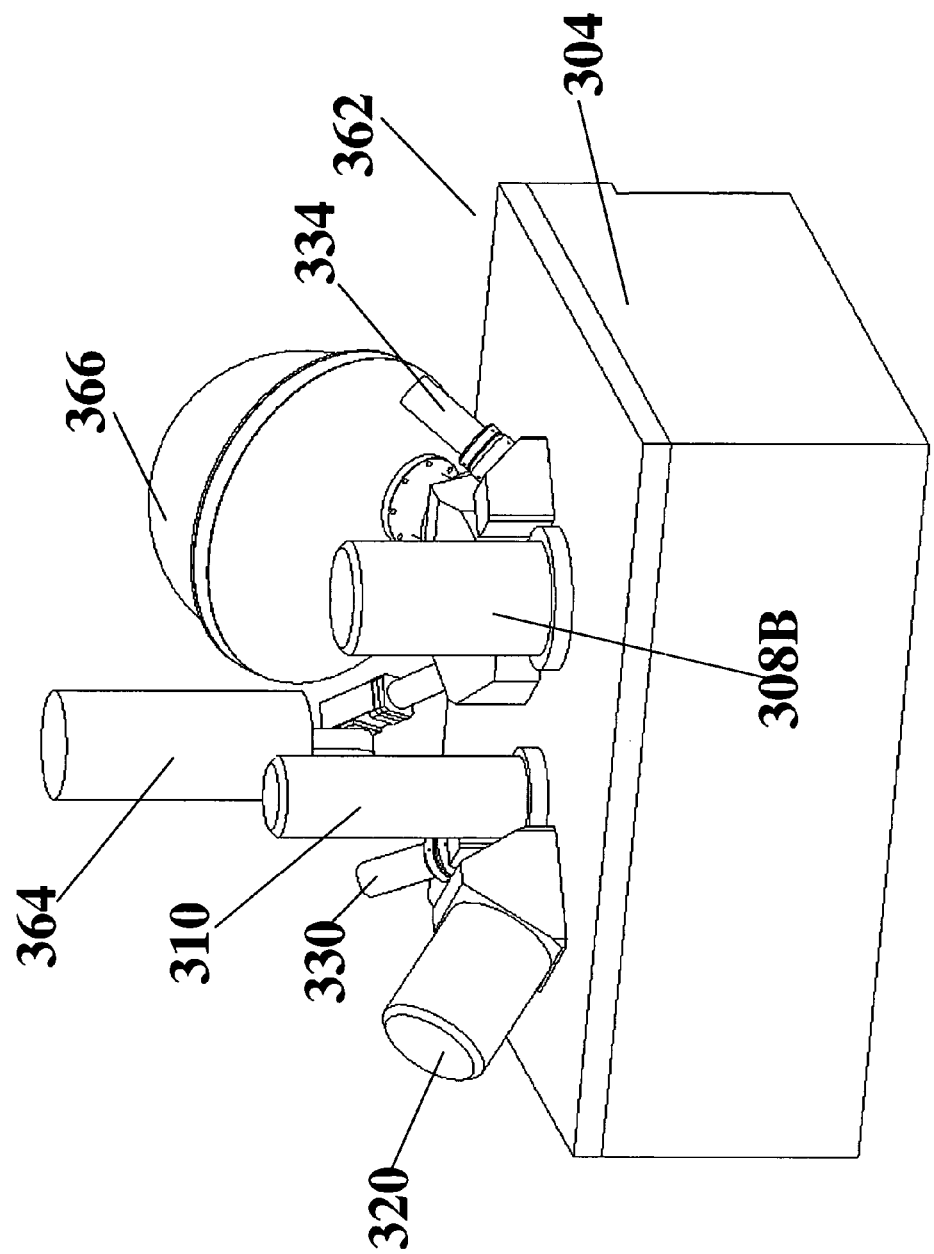
FIG. 10A provides an isometric illustrated views of a tool for sample formation and surface analysis of the formed samples according to some embodiments of the present invention.
Figure 10B:
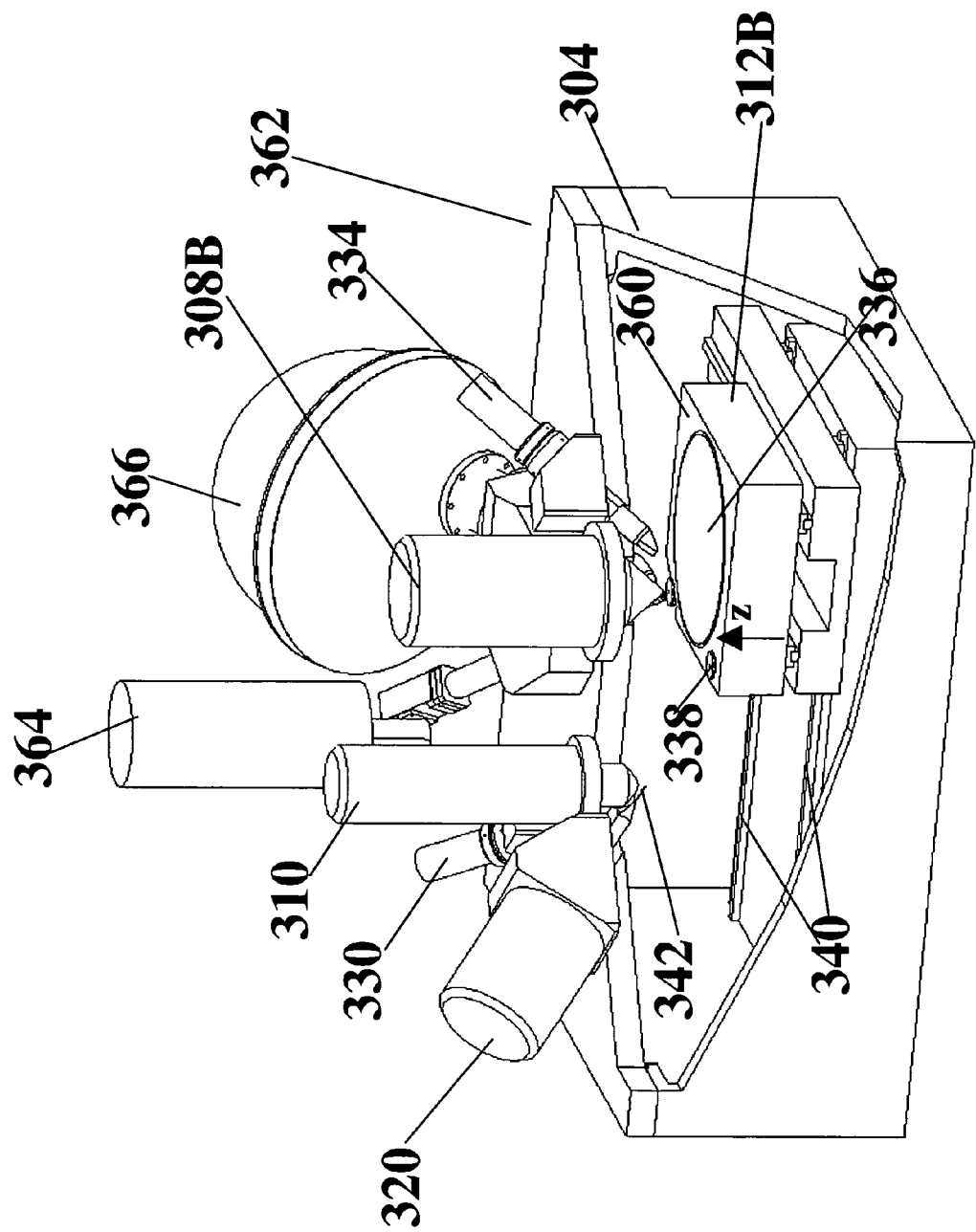
FIG. 10B-10F provide isometric broken illustrated views of a tool for sample formation and surface analysis of the formed samples according to some embodiments of the present invention.
Figure 10C:
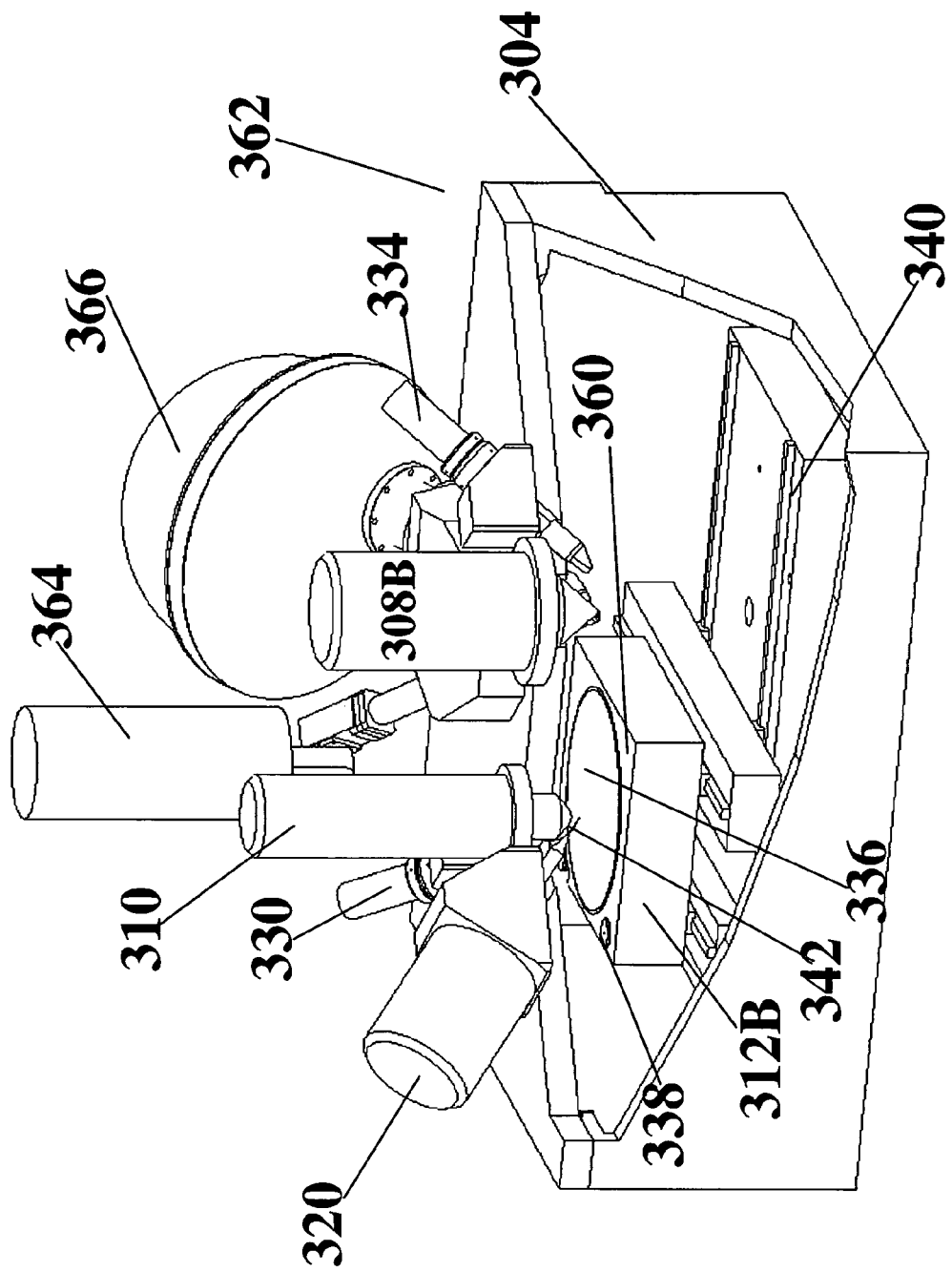
Figure 10D:
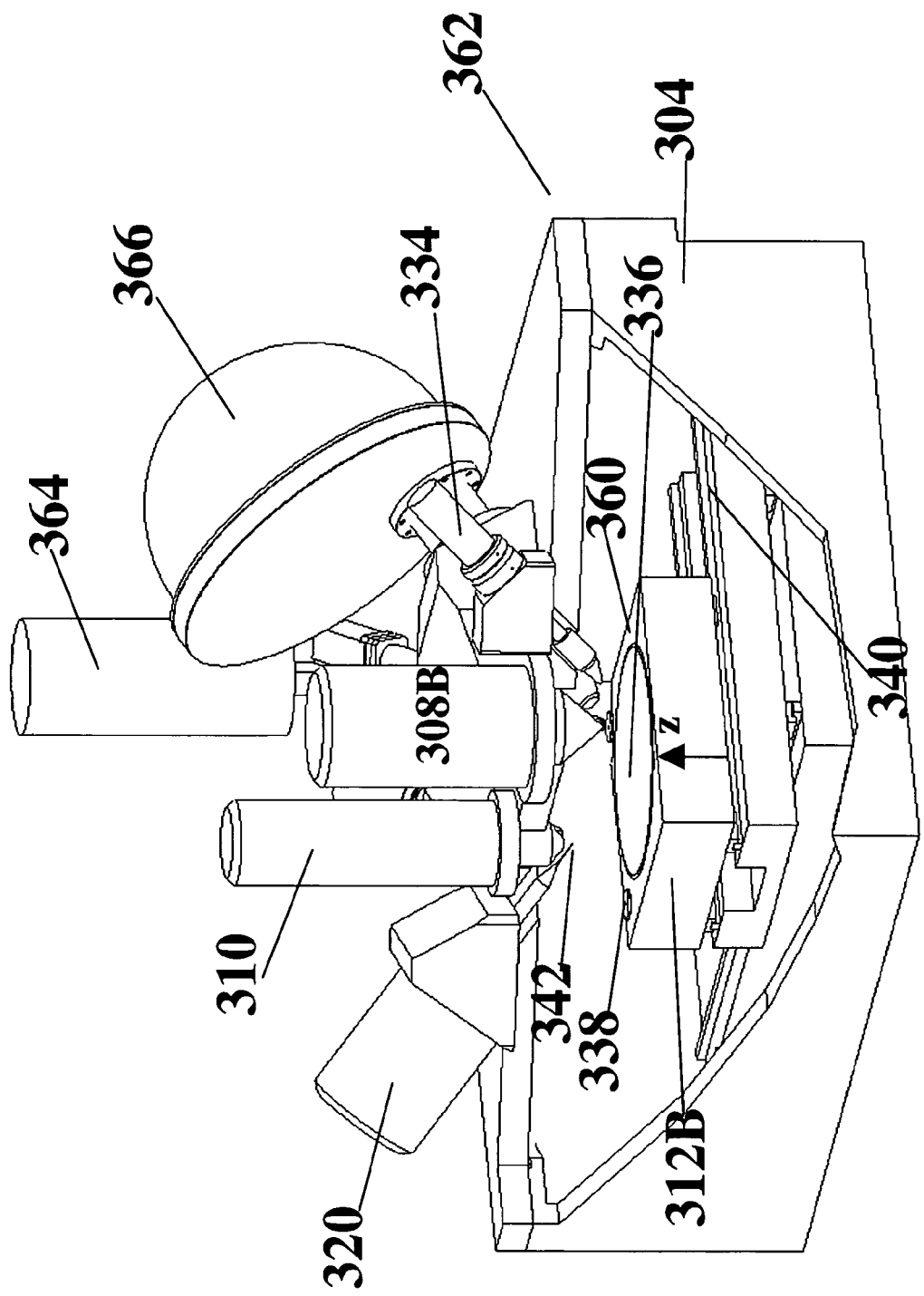

As illustrated in FIGS. 10B-C, the device includes an optional FIB detector 330 such as an ion detector or electron detector.

The multicolumn tool 362 includes a SEM detector 334 for wafer navigation.

Figure 10E:
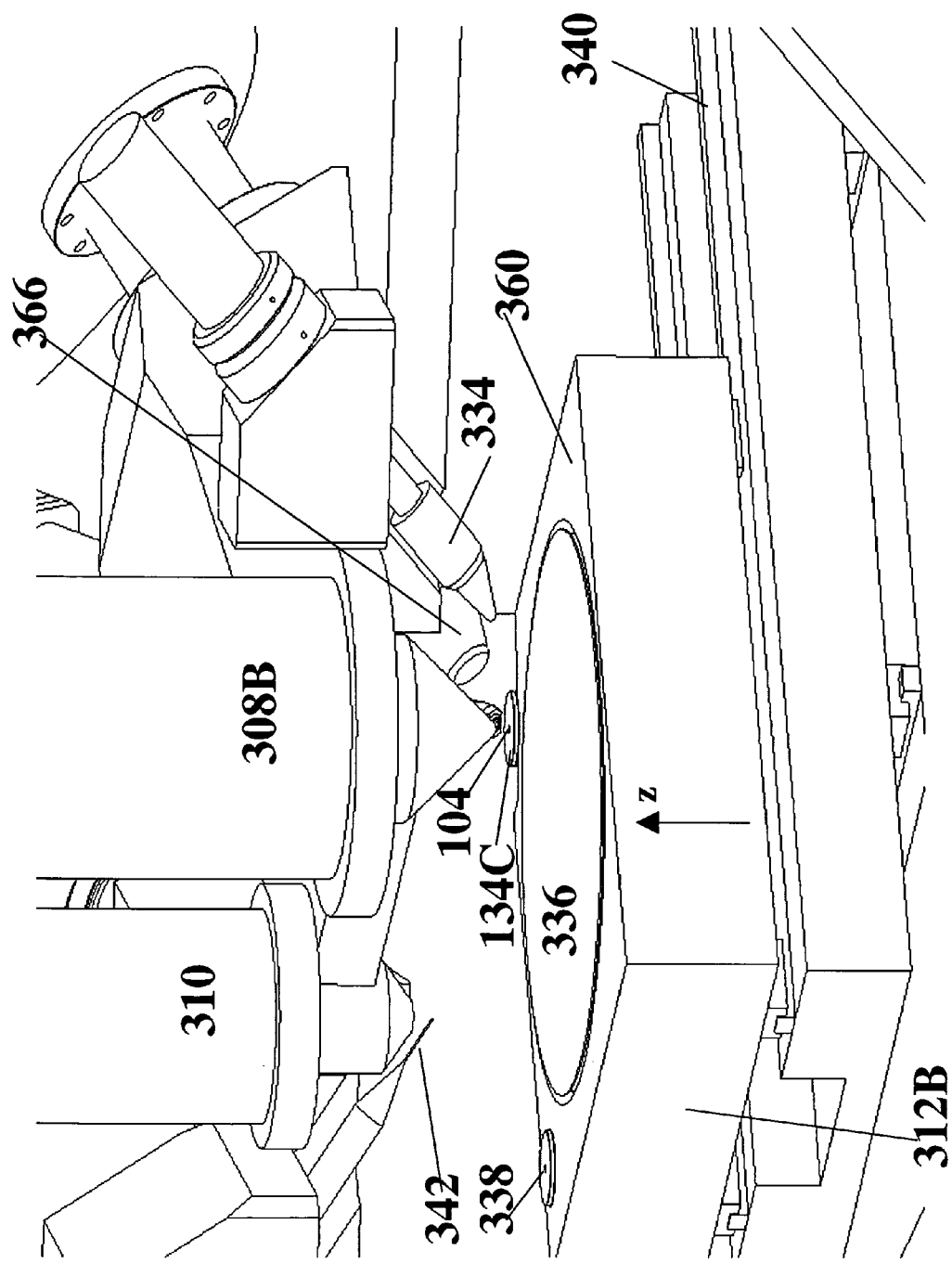
Figure 10F:
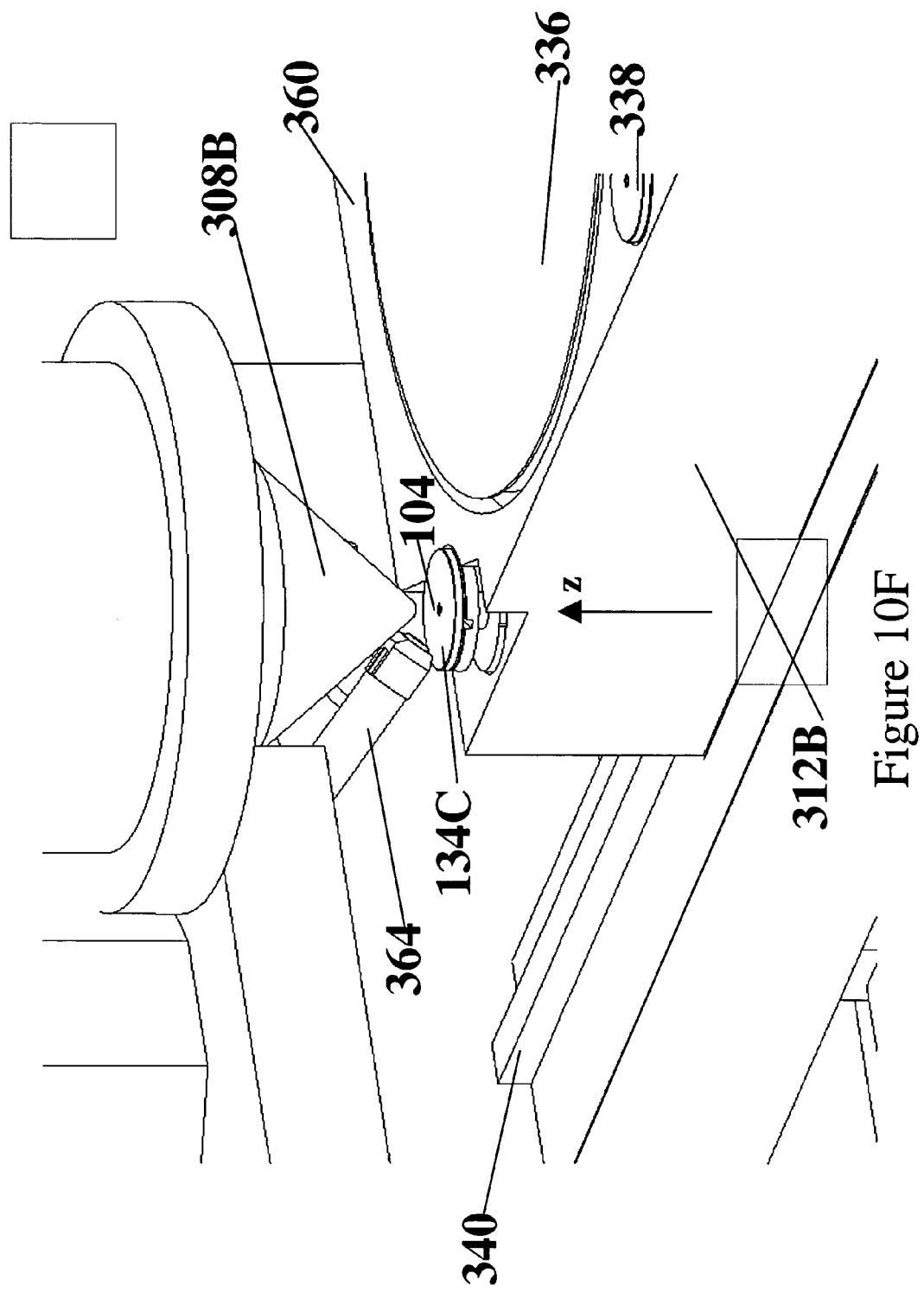

As illustrated in FIG. 10E, after extracting from the sample 104 from the wafer 336 with the needle or probe 342 of the robotic manipulator, the sample is placed on the sample support 134C for surface microanalysis using the electron beam source 308B and at least one of the auger electron detector 366 and an x-ray detector of the EDX device 364.

In particular embodiments, the second multicolumn tool 362 also includes a controller (not shown) including a processor and a memory.

In some embodiments, the process controller is programmed so that the tool executes the methods for sample formation, sample rotation, situating of sample onto a sample support, and sample surface microanalysis disclosed herein.

As illustrated in FIGS. 10A-F, the second multicolumn tool 362 lacks an electron transparency analysis device, though it is understood that such an optional electron transparency analysis device can be added to the tool 362.

Figure 11:
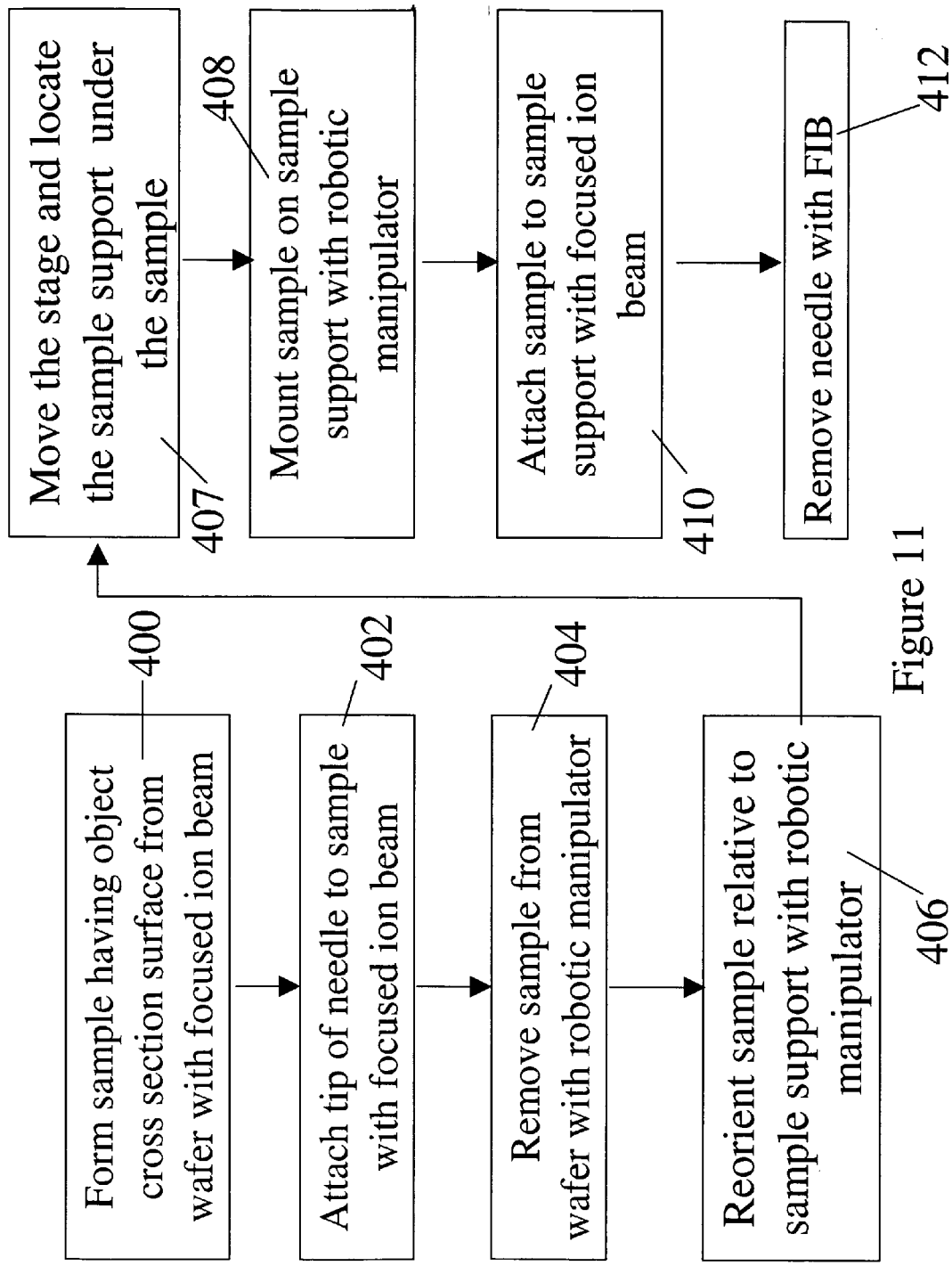
FIG. 11 provides a flow chart of sample formation, and mounting according to some embodiments of the present invention.

FIG. 11 provides a flow chart describing methods of obtaining a sample and situating this sample on a sample support according some embodiments of the invention. According to some embodiments, the methods disclosed in FIG. 11 are carried out in a single vacuum chamber, such that the vacuum chamber 304 of the multicolumn tool 322 of FIGS. 8A-E or the multicolumn tool 362 of FIGS. 10A-F, Thus, according to these embodiments, a sample 104 having an object cross section surface (120 or 122) is initially formed 400 from a wafer with focused ion beam from the FIB column 310. Subsequently, a needle or probe 128 is attached 402 to the sample 104. In some embodiments, the attaching 402 is with a focused ion beam from the FIB column 310.

The sample 104 is next removed 404 from the object 102, and reoriented 406 relative to a sample support 134 so that the outer surface 124 of the sample is substantially perpendicular to the upper surface 130 of a sample support 134. Optionally, sample 104 is rotated so that an object cross section surface is substantially parallel to the upper surface 130 of sample support 134. In some embodiments, sample 104 is rotated so that proximal object cross section surface 120 is substantially parallel to the upper surface 130 of sample support 134.

A stage such as stage 312 holding a sample support 134 is then located 407 under the sample while it is supported by the needle or the probe 128. It is noted that in some embodiments step 406 precedes step 407. Alternately, step 407 precedes step 406.

In some embodiments, the sample support 134 is supported by a stage 312.

The sample 104 is then mounted 408 on the sample support 134 with the robotic manipulator 320, and attached or welded 410 with a focused ion beam from the FIB column 310.

It is noted that in some embodiments, a sample created in a single tool or vacuum chamber is iteratively subjected to microanalysis and thinned within the single tool or vacuum chamber.

FIGS. 12A-D provide flow charts of various embodiments of an iterative method for sample forming, sample re-thinning and microanalysis in a single tool according to some embodiments of the present invention. According to embodiments depicted in FIGS. 12A-D, the formed sample is alternately subjected to microanalysis and thinned while remaining situated within a single vacuum chamber, thereby generating a series of images, wherein each image is derived from a microanalysis of a sample of a different thickness. In some embodiments, the sample is iteratively thinned and imaged after being formed from a larger object within the same vacuum chamber in which the sample is imaged.

It is understood that the process depicted in FIGS. 12A-D may be utilized independently of other aspects of the present invention described herein. In a particular embodiment, the sample is affixed to a sample support where it is alternately imaged and thinned. In a particular embodiment, this process is carried out in a single tool including both FIB and a electron microscopy device enabling electron transparency analysis.

In some embodiments, the sample re-thinning includes subjecting the sample to a focused ion beam such that the focused ion beam is incident substantially normally to an object cross-section surface of the sample.

In some embodiments, the microanalysis includes electron transparency analysis.

In some embodiments, the microanalysis includes at least one process selected from the group consisting of detection of secondary electrons, detection of backscattered electrons, and detection of photons including x-rays.

It is noted that carrying out this process in one tool eliminates the need to transfer a sample back and forth between two different tools, allowing for the automation of the process depicted in FIGS. 12A-D.

FIGS. 12A-D provides a flow chart describing some embodiments of the present invention. The process begins by forming the sample 602 in the vacuum chamber. As described in FIG. 12A, after the sample is created it is subjected to an iterative process of surface analysis 604 and surface removal by thinning 606. In some embodiments, the surface analysis 604 includes any process associated with scattering electrons off of a surface of the sample, such as SEM, EDX and detection of Auger Electrons. Optionally, the sample is subjected to optical microscopy. In some embodiments, at the time of surface analysis 604, the sample is thicker for detection of secondary electrons. According to some embodiments, at the time of surface analysis 604 no detector is required below the microanalyzed sample.

It is noted that any method known for sample thinning is appropriate for the present invention. In some embodiments, the sample is thinned 606 using a focused ion beam. In some embodiments, the surface removal by thinning is effected by a sputtering argon ion beam.

After an appropriate number of iterations of surface removal by thinning 606, the sample is thin enough for electron transparency analysis. It is understood that the "electron transparency threshold" wherein a sample becomes thin enough for electron transparency analysis is not defined in terms of a specific numerical thickness, as this number depends on a number of factors, such as the energy of the electron beam source, the nature of the material to be subjected to electron transparency analysis, and the like. Not wishing to be bound by theory, it is noted that in some instances, thinning a sample with a thickness that is the same order of magnitude as the electron transparency threshold can improve the resolution of an electron transparency analysis image.

Once the sample is sufficiently thinned it is subjected to electron transparency analysis 608. In some embodiments, a detector below the analyzed sample is required during the staged of transparency analysis 608. Furthermore, it is noted that data collection step 610A-D is illustrated as a final step in FIGS. 12A-D, though it is understood that data may be collected throughout any illustrated process.

In one exemplary embodiment, the imaged portion of a sample represents a cross section of an object such as a semiconductor wafer.

It is noted that in some embodiments the sample is subjected to more than one type of microanalysis. Furthermore, although the disclosed method is applicable to electron transparency analysis, this is not a limitation, and in some embodiments, microanalysis techniques other than electron transparency analysis are employed.

In some embodiments, the thinning includes using a FIB that selectively removes certain materials from a surface of the sample. Thus, in exemplary embodiments FIB ion milling includes introducing an interactive species such as xenon difluoride.

Figure 12A:
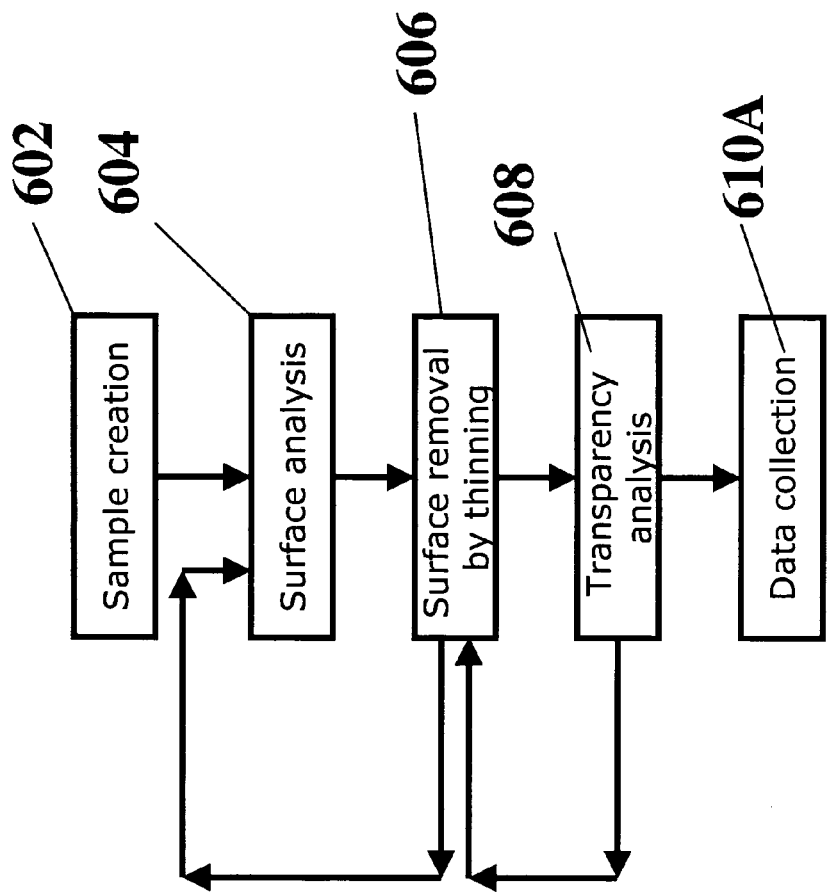
FIG. 12A-D provide flow charts of various embodiments of an iterative method for sample forming, sample re-thinning and microanalysis according to some embodiments of the invention.
Figure 12B:
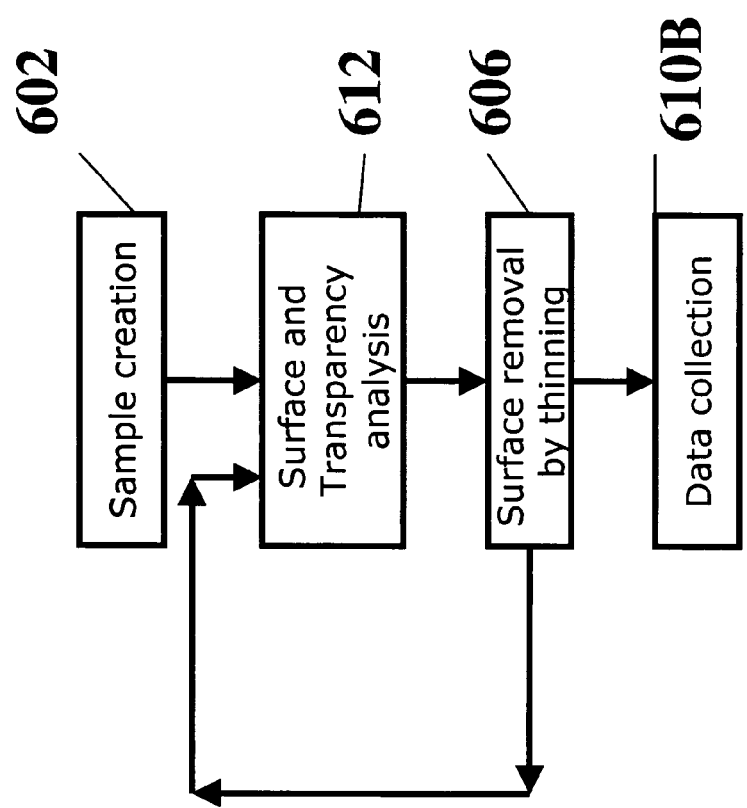

FIG. 12B provides an illustration of an alternate embodiment of the iterative process of sample re-thinning and imaging. In the embodiment depicted in FIG. 12B, a single step of microanalysis 612 entails both surface and transparency analysis.

Figure 12C:
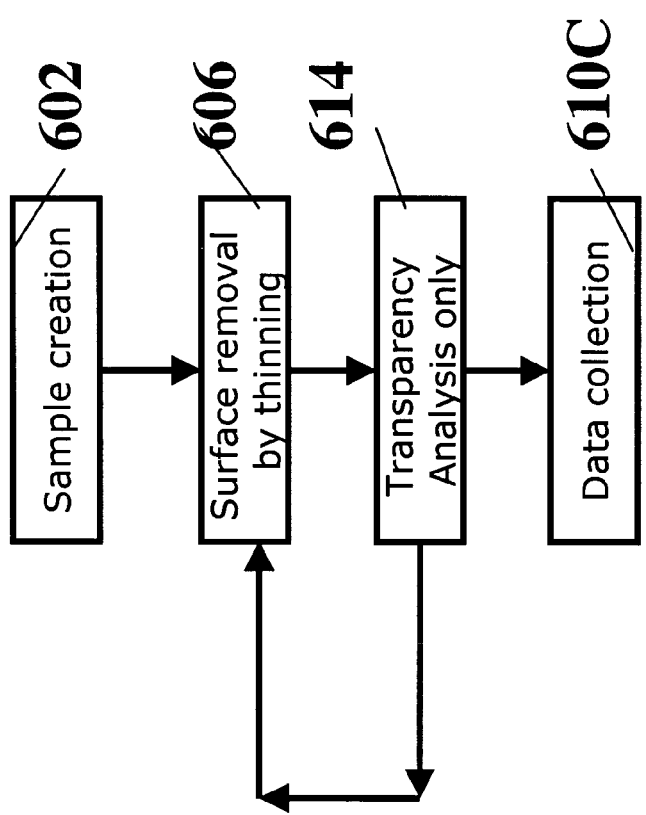

FIG. 12C provides a description of an embodiment wherein the microanalysis includes only transparency analysis.

Figure 12D:
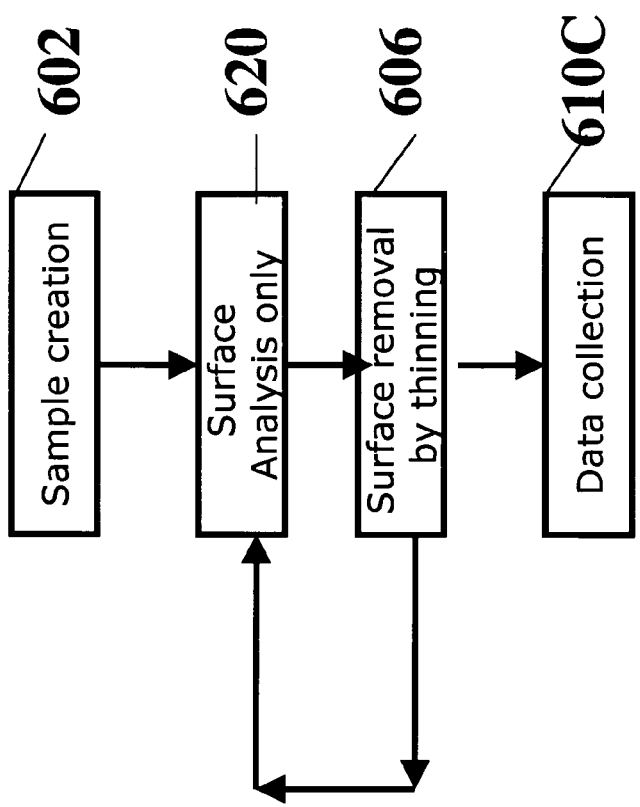

FIG. 12D provides a description of an embodiment wherein the microanalysis includes surface analysis only and excludes transparency analysis.

Figure 13:
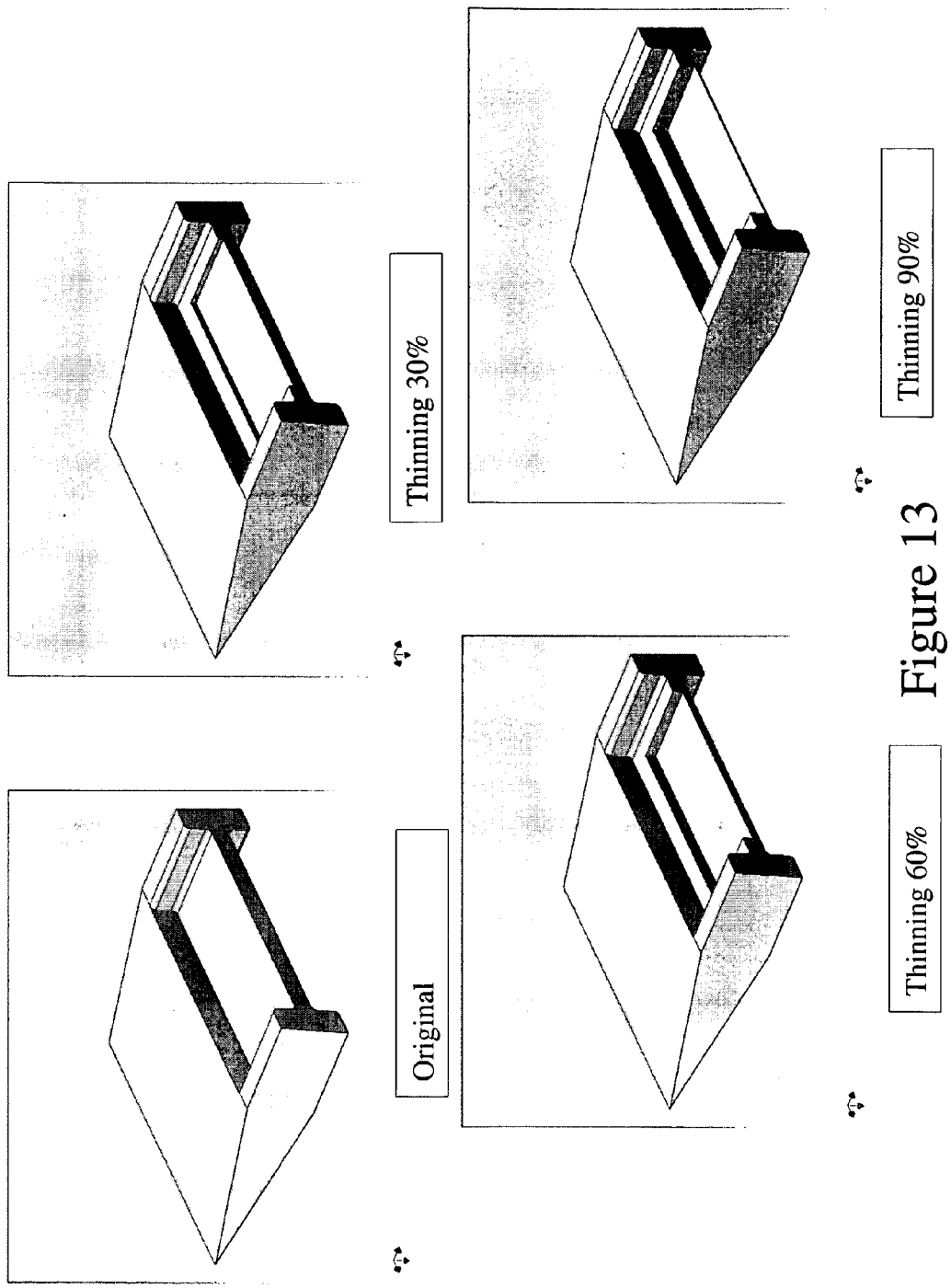
FIG. 13 provides an exemplary figure of sample thinning according to some embodiments of the present invention.

FIG. 13 provides an exemplary figure of sample thinning according to some embodiments of the present invention.

Figure 14:
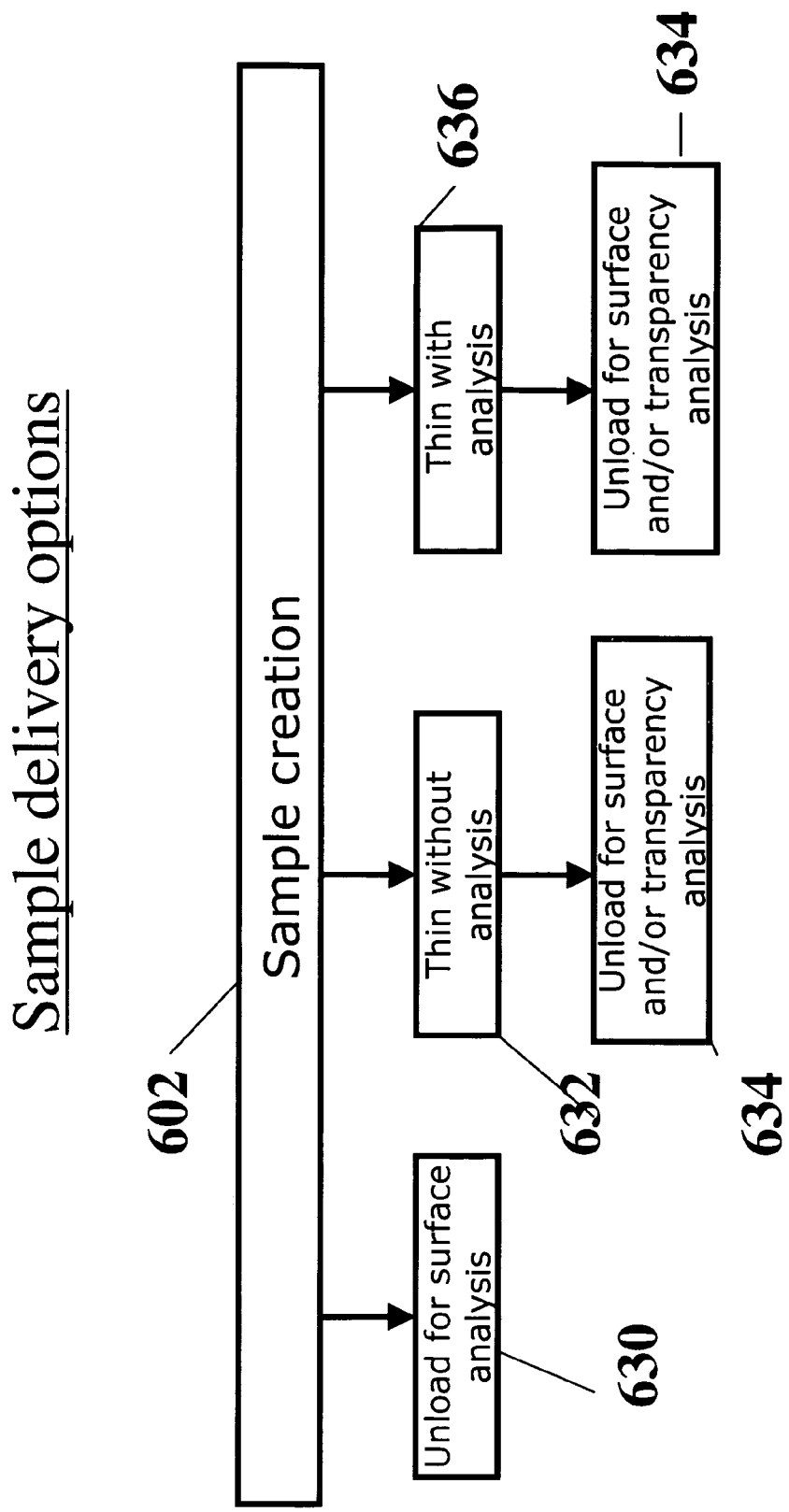
FIG. 14 provides a flowchart of various sample delivery options.

Optionally, at least one sample prepared using methods and apparatus described herein, is situated on a sample support, transferred out of the tool, and loaded onto a loading stations. FIG. 14 provides a flow chart of different sample delivery options. Thus, according to one embodiment, a created sample 602 is unloaded for surface analysis 630. Optionally, the sample is thinned with 636 or without 632 microanalysis before unloading for surface and/or transparency analysis 634. In some embodiments, the loading onto the loading station and transferring is automated, and controlled by a robotic arm (not shown), providing a fully automated process for obtaining of samples mounted to sample supports.

In the description and claims of the present application, each of the verbs, "comprise" "include" and "have", and conjugates thereof, are used to indicate that the object or objects of the verb are not necessarily a complete listing of members, components, elements or parts of the subject or subjects of the verb.

The present invention has been described using detailed descriptions of embodiments thereof that are provided by way of example and are not intended to limit the scope of the invention. The described embodiments comprise different features, not all of which are required in all embodiments of the invention. Some embodiments of the present invention utilize only some of the features or possible combinations of the features. Variations of embodiments of the present invention that are described and embodiments of the present invention comprising different combinations of features noted in the described embodiments will occur to persons of the art. The scope of the invention is limited only by the following claims.

What is claimed is:

1. A method of sample formation and imaging comprising:
   a) placing an object into a vacuum chamber;
   b) forming a sample from said object; and
   c) imaging said sample, wherein at least a portion of an electron beam traverses at least a portion of said sample, wherein said forming and imaging are carried out in said vacuum chamber.

2. The method of claim 1 wherein said object is penetrated to a depth of at most 10% of a thickness of said object during said stage of forming.

3. The method of claim 1 wherein said stage of forming includes a beam milling selected from the group consisting of ion beam milling and electron beam milling.

4. The method of claim 1 wherein said electron beam is incident substantially normally to an object cross section surface of said sample.

5. The method of claim 1 wherein said imaging includes imaging said object cross section surface.

6. The method of claim 1 wherein said sample is situated on a surface of said sample support such that an object cross section surface of said sample is substantially parallel to said surface of said sample support.

7. A method of sample formation and imaging comprising:
 a) providing an object in a vacuum chamber;
 b) forming a sample from the object inside said vacuum chamber;
 c) thinning at least a portion of the sample with an ion beam; and
 d) imaging the thinned sample, wherein at least a portion of said sample is subjected to a electron beam, wherein said thinning and imaging are repeated at least once while said sample is inside said vacuum chamber, thereby providing a plurality of images.

8. The method of claim 7 wherein said stage of forming includes a beam milling selected from the group consisting of ion beam milling and electron beam milling.

9. The method of claim 7 wherein said imaging includes imaging an object cross section surface of the sample.

10. The method of claim 7 wherein at least one said stage of imaging includes detecting photons.

11. The method of claim 7 wherein said thinning and imaging are repeated at least once until said at least a portion of said sample is eliminated by said thinning.

12. The method of claim 7 wherein said stage of thinning includes subjecting said sample to at least one ion beam selected from the group consisting of a focused ion beam and a beam of argon ions.

13. The method of claim 7 wherein said thinning includes selective removal of material.

14. The method of claim 7 wherein said thinning includes subjecting said sample to a particle beam incident substantially normally to said object cross section surface, said particle beam selected from the group consisting of an ion beam and electron beam.

* * * * *